US007041472B2

(12) United States Patent
Norioka et al.

(10) Patent No.: US 7,041,472 B2
(45) Date of Patent: May 9, 2006

(54) METHOD FOR SELECTIVELY COLLECTING N-TERMINAL PEPTIDE FRAGMENT OF PROTEIN

(75) Inventors: Shigemi Norioka, Ibaraki (JP); Norikazu Ueyama, Osaka (JP); Taka-aki Okamura, Osaka (JP); Takashi Nakazawa, Nara (JP); Minoru Yamaguchi, Kyoto (JP); Eiji Ando, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 100 days.

(21) Appl. No.: 10/739,111

(22) Filed: Dec. 19, 2003

(65) Prior Publication Data

US 2004/0152155 A1    Aug. 5, 2004

(30) Foreign Application Priority Data

Dec. 25, 2002   (JP) .............................. 2002-375399

(51) Int. Cl.
    *C12P 21/06*   (2006.01)

(52) U.S. Cl. .................................... 435/68.1

(58) Field of Classification Search ............... 435/7.1, 435/68.1, 287.2; 702/19; 530/417
See application file for complete search history.

(56) References Cited

U.S. PATENT DOCUMENTS

2004/0005633 A1 *  1/2004  Vandekerckhove et al. .. 435/7.1

FOREIGN PATENT DOCUMENTS

WO    WO 02/095412    * 11/2002

OTHER PUBLICATIONS

Gygi et al., quantitative analysis of complex protein mixtures using isotope-coded affinity tags, Oct. 1999, Nature Biotechnology, vol. 17, pp. 994-999.*
W.J. Henzel et al., "Identifying Proteins from Two-dimensional Gels by Molecular Mass Searching of Peptide Fragments in Protein Sequence Database", Proceedings of the National Academy of Sciences of the United States of America 90 (1993): pp. 5011-5015.

(Continued)

*Primary Examiner*—Jon Weber
*Assistant Examiner*—Robert B. Mondesi
(74) *Attorney, Agent, or Firm*—Rader, Fishman & Grauer PLLC

(57) ABSTRACT

The present invention provides a method for selectively collecting the N-terminal peptide fragments of a protein of interest whether or not the protein of interest is modified on the N-terminus. A method for selectively collecting the N-terminal peptide fragment of a protein, comprising: a protection step (1) of protecting side chain-amino groups of amino acid residues containing side chain-amino groups of a protein of interest to obtain a protected protein protected on the side chain-amino groups; a fragmentation step (2) of cleaving the protected protein into one N-terminal peptide fragment (a) containing the N-terminus of the peptide of interest and one or more of peptide fragments (b) other than the N-terminal peptide fragment (a); and a separation step (3) of separating the N-terminal peptide fragment (a) from the other peptide fragments (b) by selectively eluting the N-terminal peptide fragment (a) based on the difference in their reactivity or affinity to substrate, wherein the selective elution is achieved either by allowing the other peptide fragments (b) to bind to the substrate while allowing the N-terminal peptide fragment (a) to elute, or by allowing the N-terminal peptide fragment (a) to bind to the substrate while allowing the other peptide fragments (b) to elute and subsequently eluting the bound N-terminal peptide fragment (a).

25 Claims, 10 Drawing Sheets

OTHER PUBLICATIONS

Peter James et al., "Protein Identification by Mass Profile Fingerprinting", Biochemical and Biophysical Research Communications 195 (1993): pp. 58-64.

D.F. Hunt et al., "Protein Sequencing by Tandem Mass Spectrometry", Proceedings of the National Academy of Sciences of the United States of America 83 (1986): pp. 6233-6237.

* cited by examiner

SEQUENCE LISTING

<160> NUMBER OF SEQ ID NOS: 5

<210> SEQ ID NO 1
<211> LENGTH: 13
<212> TYPE: PRT
<213> ORGANISM: Human
<220> FEATURE:
<221> NAME/KEY: MOD_RES
<222> LOCATION: 1
<223> OTHER INFORMATION: PYRROLIDONE CARBOXYLIC ACID

<400> SEQUENCE: 1

Glu Leu Tyr Glu Asn Lys Pro Arg Arg Pro Tyr Ile Leu
 1               5                  10

<210> SEQ ID NO 2
<211> LENGTH: 8
<212> TYPE: PRT
<213> ORGANISM: Human
<220> FEATURE:
<221> NAME/KEY: MOD_RES
<222> LOCATION: 1
<223> OTHER INFORMATION: PYRROLIDONE CARBOXYLIC ACID

<400> SEQUENCE: 2

Glu Leu Tyr Glu Asn Lys Pro Arg
 1               5

<210> SEQ ID NO 3
<211> LENGTH: 5
<212> TYPE: PRT
<213> ORGANISM: Human

<400> SEQUENCE: 3

Arg Pro Tyr Ile Leu
 1               5

<210> SEQ ID NO 4
<211> LENGTH: 5
<212> TYPE: PRT
<213> ORGANISM: Artificial Sequence
<220> FEATURE:
<223> OTHER INFORMATION: Peptide Fragment
<220> FEATURE:
<221> NAME/KEY: BINDING
<222> LOCATION: 1
<223> OTHER INFORMATION: Peptide bond formation by using biotinyl
      cysteic acid
<220> FEATURE:
<221> NAME/KEY: BINDING
<222> LOCATION: 1
<223> OTHER INFORMATION: Guanidination

<400> SEQUENCE: 4

Lys Val Phe Gly Arg
 1               5

<210> SEQ ID NO 5
<211> LENGTH: 16
<212> TYPE: PRT
<213> ORGANISM: Artificial Sequence
<220> FEATURE:
<223> OTHER INFORMATION: Peptide Fragment
<220> FEATURE:
<221> NAME/KEY: BINDING
<222> LOCATION: 1
<223> OTHER INFORMATION: Acetylation
<220> FEATURE:

-continued

```
<221> NAME/KEY: BINDING
<222> LOCATION: 11
<223> OTHER INFORMATION: Carbamoylmethylation
<220> FEATURE:
<221> NAME/KEY: BINDING
<222> LOCATION: 16
<223> OTHER INFORMATION: Guanidination

<400> SEQUENCE: 5

Gly Ser Ile Gly Ala Ala Ser Met Glu Phe Cys Phe Asp Val Phe Lys
 1               5                  10                  15
```

METHOD FOR SELECTIVELY COLLECTING N-TERMINAL PEPTIDE FRAGMENT OF PROTEIN

BACKGROUND OF THE INVENTION

1. Field of the Invention

The present invention relates to a method for collecting N-terminus of protein that is useful in determining protein amino acid sequence.

2. Disclosure of the Related Art

One way to determine the amino acid sequence of a protein is by protein sequencers. In sequencing a protein using a typical protein sequencer, an N-terminus labeled protein is subjected to Edman method to cleave and remove the N-terminal amino acid one at a time. The removed amino acid is converted to a more stable form. The obtained end product is then detected by UV and determined based on the retention time in high performance liquid chromatography (HPLC). In this manner, the amino acid sequence of a protein can be determined sequentially from its N-terminus. However, the protein sequencing using protein sequencers has several drawbacks. First, Edman method cannot be applied to any protein with modified N-terminus, resulting in failure of directly sequencing. Although the protein with modified N-terminus can be sequenced indirectly by first making it into fragments, such an approach only permits the determination of the internal sequence of the protein, but not the sequencing from the N-terminus. Second, in Edman method, the side reactions caused by the low stability of the end product and the like often make HPLC analysis difficult. Third, the low UV-absorbance of the end product of Edman method can lead to low sensitivity.

In recent years, mass spectrometers with extremely high sensitivity and accuracy have been developed and the data obtained by mass spectroscopy analysis alone can permit effective, reliable determination of partial amino acid sequences of a peptide and what protein a peptide originates from. For this reason, mass spectroscopy has become a major tool in protein analysis. In mass spectroscopy-based protein analysis, a protein is cleaved into peptide fragments by enzymatically digestion and the like, and masses of the peptide fragments are measured. By comparing this obtained data with the sequence data stored in a database, the identity of the protein is determined. Among such mass spectroscopic techniques are peptide mass fingerprinting (PMF) (See, for example, Henzel W J., Billeci T M., Stults J T., Wong S C., Grimley C., and Watanabe C. "Identifying proteins from two-dimensional gels by molecular mass searching of peptide fragments in protein sequence databases." *Proceedings of the National Academy of Sciences of the United States of America* 90 (1993): 5011–5015, and, James P., Quadroni M., Carafoli E., and Gonnet G. "Protein identification by mass profile finger printing." *Biochemical Biophysical Research Communications* 195 (1993): 58–64), and, MS/MS analysis for directly obtaining the information concerning the amino acid sequence of a peptide (See, for example, Hunt D F., Yates J R., Shabanowitz J., Winston S., and Hauer C H. "Protein sequencing by tandem mass spectrometry" *Proceedings of the National Academy of Sciences of the United States of America* 83 (1986): 6233–6237). However, none of these techniques are capable of distinguishing between the N-terminal peptide fragment and the other peptide fragments of a protein. Therefore, these techniques only allow the determination of internal amino acid sequences of a protein, but not the sequencing from the N-terminus of a protein.

SUMMARY OF THE INVENTION

Accordingly, it is an objective of the present invention to provide a method for selectively collecting N-terminal peptide fragments of a protein of interest so that the sequence from N-terminus of the protein can be determined by mass spectroscopic analysis. The method can collect N-terminal peptide fragments whether or not the N-terminus of the protein is modified.

In the course of studies, the present inventors have discovered that the above-mentioned objective is achieved by first guanidinating the side-chain amino groups of amino acid residues containing side-chain amino groups, such as lysine, of the protein of interest, then cleaving the guanidinated protein into fragments, and then separating N-terminal peptide fragment containing the N-terminus of the protein of interest from the other peptide fragments by taking advantage of the difference in the reactivity or the affinity of the peptide fragments to substrate. The discovery ultimately led the present inventors to devise the present invention.

The present invention comprises the following inventions:

<1> A method for selectively collecting the N-terminal peptide fragment of a protein, comprising:

a protection step (1) of protecting side chain-amino groups of amino acid residues containing side chain-amino groups of a protein of interest to obtain a protected protein protected on the side chain-amino groups;

a fragmentation step (2) of cleaving the protected protein into one N-terminal peptide fragment (a) containing the N-terminus of the peptide of interest and one or more of peptide fragments (b) other than the N-terminal peptide fragment (a); and a separation step (3) of separating the N-terminal peptide fragment (a) from the other peptide fragments (b) by selectively eluting the N-terminal peptide fragment (a) based on the difference in their reactivity or affinity to substrate, wherein the selective elution is achieved either by allowing the other peptide fragments (b) to bind to the substrate while allowing the N-terminal peptide fragment (a) to elute, or by allowing the N-terminal peptide fragment (a) to bind to the substrate while allowing the other peptide fragments (b) to elute and subsequently eluting the bound N-terminal peptide fragment (a).

The term "protein" as used herein encompasses oligopeptides, polypeptides and other types of peptide.

<2> A method for selectively collecting the N-terminal peptide fragment of a protein, comprising:

a fragmentation step (2') of cleaving a protein of interest into one N-terminal peptide fragment (a') and one or more of peptide fragments (b') other than the N-terminal peptide fragment (a');

a protection step (1') of protecting side chain-amino groups of amino acid residues containing side chain-amino group of the N-terminal peptide fragment (a') and the other peptide fragments (b') to obtain a protected N-terminal peptide fragment (a) protected on the side chain-amino groups, along with the other protected polypeptide fragments (b) protected on the side chain-amino groups; and a separation step (3) of separating the N-terminal peptide fragment (a) from the other peptide fragments (b) by selectively eluting the N-terminal peptide fragment (a) based on the difference in their reactivity or affinity to substrate, wherein the selective elution is achieved either by allowing the other peptide fragments (b) to bind to the substrate while allowing the N-terminal peptide fragment (a) to elute, or by allowing the N-terminal peptide fragment (a) to bind to the substrate while allowing the other peptide fragments (b) to elute and subsequently eluting the bound N-terminal peptide fragment (a).

<3> The method according to <1>, comprising:

a guanidination step (1) of guanidinating side chain-amino groups of amino acid residues containing side chain-amino groups of a protein of interest to obtain a guanidinated protein in which the side chain-amino groups have been converted to guanidino groups;

a fragmentation step (2) of cleaving the guanidinated protein into one N-terminal peptide fragment (a) containing the N-terminus of the peptide of interest and one or more of peptide fragments (b) other than the N-terminal peptide fragment (a); and a separation step (3) of separating the N-terminal peptide fragment (a) from the other peptide fragments (b) by selectively eluting the N-terminal peptide fragment (a) based on the difference in their reactivity or affinity to substrate, wherein the selective elution is achieved either by allowing the other peptide fragments (b) to bind to the substrate while allowing the N-terminal peptide fragment (a) to elute, or by allowing the N-terminal peptide fragment (a) to bind to the substrate while allowing the other peptide fragments (b) to elute and subsequently eluting the bound N-terminal peptide fragment (a).

<4> The method according to <2>, comprising:

a fragmentation step (2') of cleaving a protein of interest into one N-terminal peptide fragment (a') and one or more of peptide fragments (b') other than the N-terminal peptide fragment (a');

a protection step (1') of guanidinating side chain-amino groups of amino acid residues containing side chain-amino groups of the N-terminal peptide fragment (a') and the other peptide fragments (b') to obtain a guanidinated N-terminal peptide fragment (a) in which the side chain-amino groups have been converted to guanidino groups, along with the other guanidinated polypeptide fragments (b) in which the side chain-amino groups have been converted to guanidino groups; and a separation step (3) of separating the N-terminal peptide fragment (a) from the other peptide fragments (b) by selectively eluting the N-terminal peptide fragment (a) based on the difference in their reactivity or affinity to substrate, wherein the selective elution is achieved either by allowing the other peptide fragments (b) to bind to the substrate while allowing the N-terminal peptide fragment (a) to elute, or by allowing the N-terminal peptide fragment (a) to bind to the substrate while allowing the other peptide fragments (b) to elute and subsequently eluting the bound N-terminal peptide fragment (a).

<5> The method according to <3>, wherein the protein of interest is a protein modified on the N-terminal and the separation step (3) is achieved by allowing the other peptide fragments (b) to bind to the substrate while allowing the N-terminal peptide fragment (a) to elute.

<6> The method according to <5>, wherein the substrate comprises a molecule or part of a molecule that can chemically react with an amino group to form a covalent bond.

<7> The method according to <6>, wherein the substrate is selected from the group consisting of p-phenylene diisothiocyanate (DITC) polymer resin, and allylamine polymer resin.

As used herein, the term "DITC polymer resin" refers to a resin immobilized with plural of DITC molecules thereon and the term "allylamine polymer resin" refers to resin immobilized with plural of allylamine molecules thereon.

<8> The method according to <5>, further including, after the fragmentation step (2) or the guanidination step (1') and before the separation step (3), the step of coupling an affinity compound with the N-terminuses of the other peptide fragments (b), the affinity compound capable of specifically binding to a particular molecule or a particular part of a molecule to form a complex, wherein the substrate includes an immobilized ligand comprising the particular molecule or the particular part of the molecule.

<9> The method according to <8>, wherein the affinity compound is an antigen and the ligand is an antibody against the antigen.

<10> The method according to <8>, wherein the affinity compound is a biotin derivative and the ligand is an avidin.

<11> The method according to <4>, wherein the protein of interest is a protein modified on the N-terminus and the separation step (3) is achieved by allowing the other peptide fragments (b) to bind to the substrate while allowing the N-terminal peptide fragment (a) to elute.

<12> The method according to <11>, wherein the substrate comprises a molecule or part of a molecule that can chemically react with an amino group to form a covalent bond.

<13> The method according to <12>, wherein the substrate is selected from the group consisting of p-phenylene diisothiocyanate (DITC) polymer resin, and allylamine polymer resin.

<14> The method according to <11>, further including, after the fragmentation step (2) or the guanidination step (1') and before the separation step (3), the step of coupling an affinity compound with the N-terminuses of the other peptide fragments (b), the affinity compound capable of specifically binding to a particular molecule or a particular part of a molecule to form a complex, wherein the substrate includes an immobilized ligand comprising the particular molecule or the particular part of the molecule.

<15> The method according to <14>, wherein the affinity compound is an antigen and the ligand is an antibody against the antigen.

<16> The method according to <14>, wherein the affinity compound is a biotin derivative and the ligand is an avidin.

<17> The method according to <3>, wherein the protein of interest is a protein with unmodified N-terminus and the method further includes, after the guanidination step (1) and before the fragmentation step (2), the step of modifying the unmodified N-terminus of the protein of interest.

<18> The method according to <17>, wherein the unmodified N-terminus of the protein of interest is modified with an affinity compound that can specifically bind to a particular molecule or a particular part of a molecule to form a complex.

<19> The method according to <18>, wherein the substrate comprises an immobilized ligand comprising the particular molecule or the particular part of the molecule, and the separation step (3) is achieved by allowing the N-terminal peptide fragment (a) to bind to the substrate while allowing the other peptide fragments (b) to elute and subsequently eluting the bound N-terminal peptide fragment (a).

<20> The method according to <19>, wherein the affinity compound is an antigen and the ligand is an antibody against the antigen.

<21> The method according to <19>, wherein the affinity compound is a biotin derivative and the ligand is an avidin.

<22> The method according to <18>, wherein the substrate comprises a molecule or a part of a molecule that can chemically react with an amino group to form a covalent bond, and the separation step (3) is achieved by allowing the other peptide fragments (b) to bind to the substrate while allowing the N-terminal peptide fragment (a) to elute.

<23> The method according to <22>, wherein the substrate is selected from the group consisting of p-phenylene diisothiocyanate (DITC) polymer resin, and allylamine polymer resin.

<24> The method according to <17>, wherein the unmodified N-terminus of the protein of interest is modified with a compound other than the affinity compounds that can specifically bind to a particular molecule or a particular part of a molecule to form a complex, and the separation step (3) is achieved by allowing the other peptide fragments (b) to bind to the substrate while allowing the N-terminal peptide fragment (a) to elute.

<25> The method according to <24>, wherein the substrate comprises a molecule or part of a molecule that can chemically react with an amino group to form a covalent bond.

<26> The method according to <25>, wherein the substrate is selected from the group consisting of p-phenylene diisothiocyanate (DITC) polymer resin, and allylamine polymer resin.

<27> The method according to <24>, further including, after the fragmentation step (2) and before the separation step (3), the step of coupling an affinity compound with the N-terminuses of the other peptide fragments (b), the affinity compound capable of specifically binding to a particular molecule or a particular part of a molecule to form a complex, wherein the substrate includes an immobilized ligand comprising the particular molecule or the particular part of the molecule.

<28> The method according to <27>, wherein the affinity compound is an antigen and the ligand is an antibody against the antigen.

<29> The method according to <27>, wherein the affinity compound is a biotin derivative and the ligand is an avidin.

According to the present invention, there is provided a method for selectively collecting the N-terminal peptide fragments of a protein of interest. The method allows the selective collection of the N-terminal peptide fragments whether or not the protein of interest is modified on the N-terminus and, thus, the invention allows the sequencing from the N-terminus in the mass-spectrometry-based protein sequencing.

DETAILED DESCRIPTION OF THE INVENTION

The method of the present invention comprises a protection step, a fragmentation step and a separation step. In one embodiment, the protection step (1) comes first, followed by the fragmentation step (2) and then the separation step (3). In an alternative embodiment, the order of the protection step (1) and the fragmentation step (2) is reversed: a fragmentation step (2') comes first, followed by a protection step (1') and then the separation step (3).

In the protection step (1), side chain-amino groups of amino acid residues containing side chain-amino groups of a protein of interest are protected to obtain suitably protected protein. In the subsequent fragmentation step (2), the protected protein obtained in the step (1) is cleaved into an N-terminal peptide fragment (a) containing the N-terminus of the protein of interest and the other peptide fragments (b).

On the other hand, in the fragmentation step (2'), a protein of interest is first cleaved into an N-terminal peptide fragment (a') and the other peptide fragments (b'). This is followed by the protection step (1') in which side chain-amino groups of amino acid residues containing side chain-amino groups of the peptide fragments (a') and (b') are protected to obtain an N-terminal peptide fragment (a) and the other peptide fragments (b).

In the separation step (3), the N-terminal peptide fragment (a) obtained by the step (2) or (1') is separated from the other peptide fragments (b) by taking advantage of the difference in the reactivity or the affinity to substrate. Specifically, either one of the N-terminal peptide fragment (a) or the other peptide fragments (b) is allowed to bind to substrate while the other is eluted.

One way to protect the side chain-amino groups of amino acid residues containing side chain-amino groups in the protection step is guanidination. Taking this process as an example, one embodiment of the method of the present invention will now be described in detail.

Described first is the case in which the N-terminus of a protein of interest has been modified. When a protein of interest has a modified N-terminus, a guanidination step (1A) is first carried out, followed by a fragmentation step (2A) and then a separation step (3A). The order of the step (1A) and the step (2A) may be reversed. Specifically, a fragmentation step (2A') may precede a guanidination step (1A'), which is followed by the same separation step (3A).

Figure 1:
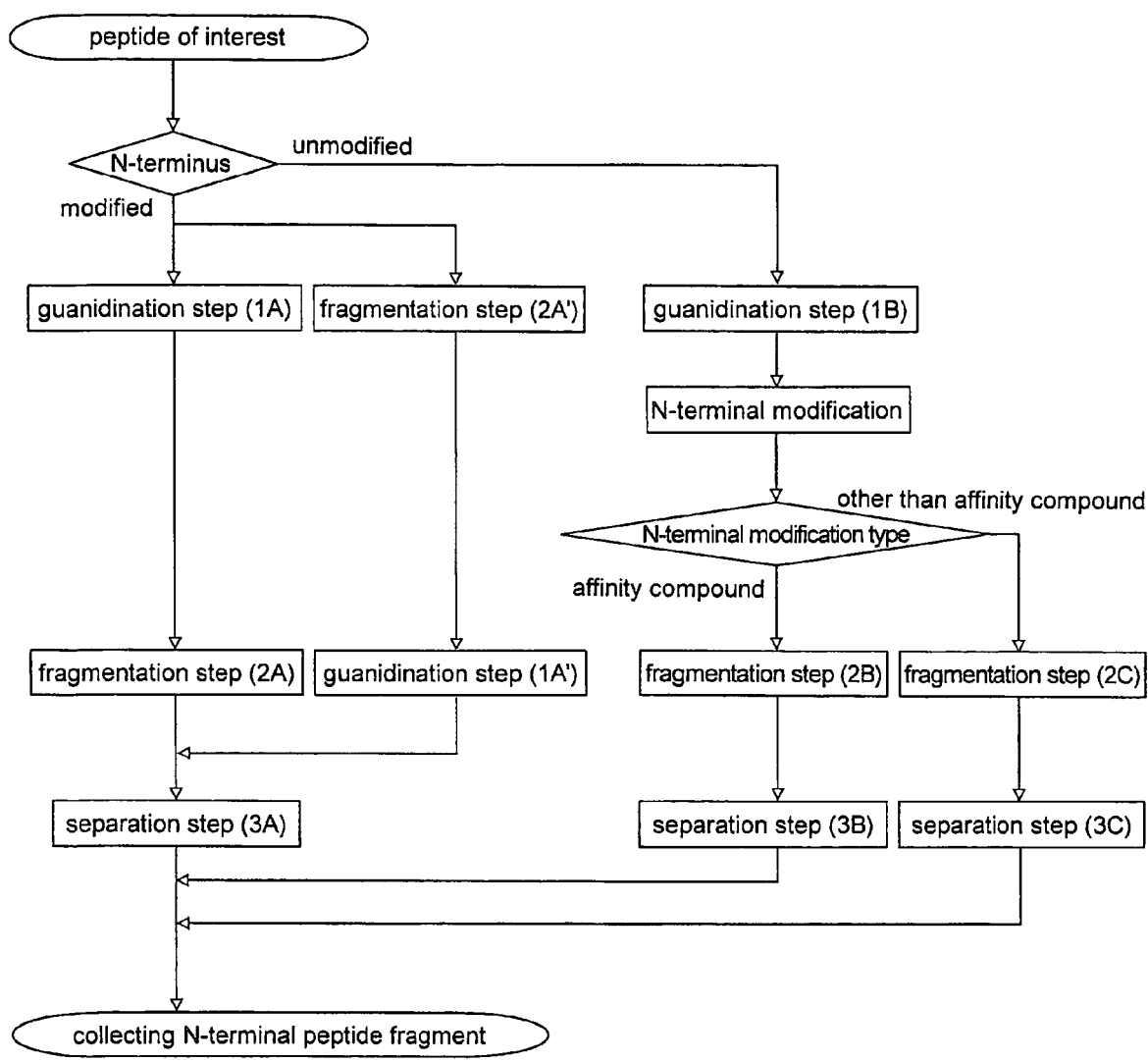
FIG. 1 is a flow-chart showing methods in accordance with the present invention.

The method of the present invention is shown by a flow chart in FIG. 1. Each step of the method is described in the following with reference to FIG. 1.

[Guanidination Step (1A)]

First, the side chain-amino groups of amino acid residues containing side chain-amino group of a protein of interest are protected. Examples of the amino acid residues containing side chain-amino groups include lysine group, which has an ε-amino group, and ornithine group, which has a δ-amino group. In general, these side chain-amino groups are protected by guanidination, which converts lysine residues into homoarginine residues and ornithine residues into arginine residues.

The step is shown, for example, in the scheme 1 below, which depicts a protein model that contains only lysine residues as the amino acid residue containing side chain-amino group. In the scheme 1, $R_1$ represents a modifying group on the N-terminus of a protein of interest and letters a through i each represent an amino acid residue that does not contain an amino group in their side chains.

[Scheme 1]

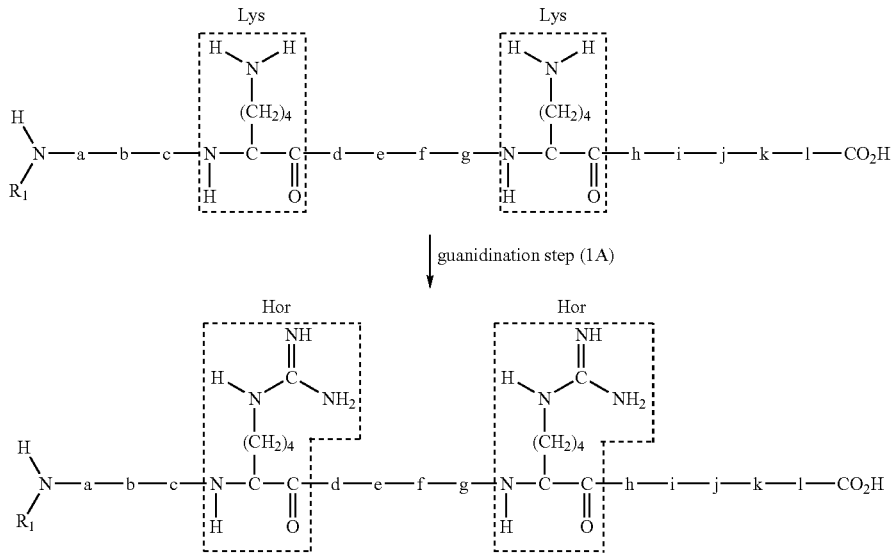

As shown in the scheme 1, a side chain-amino group (—$NH_2$) is converted to a guanidino group (—NHC(=NH)$NH_2$) in the guanidination reaction. Typical guanidination reagents include o-methylisourea, s-methylisourea, 1-guanyl-3,5-dimethylpyrazole. In practice, a protein of interest and a guanidination reagent are mixed and reacted in a basic solution such as an aqueous ammonia solution. In this manner, a guanidinated protein, in which the side chain-amino groups have been converted to guanidino groups, may be obtained.

[Fragmentation Step (2A)]

The resulting guanidinated protein is then cleaved into fragments. This can be carried out by chemical fragmentation or enzymatic digestion and the like. Chemical fragmentation may be carried out by using BrCN.

For enzymatic digestion, endoproteases may be used. In the present invention, a suitable enzyme that generates N-terminal peptide fragments with the size readily analyzed by a mass-spectrometer can be selected depending on the protein of interest. For example, trypsin, chymotrypsin, or Glu-C and the like may preferably be used. The enzymatic digestion may be carried out by using known techniques. The step is shown, for example, in the following scheme 2:

[Scheme 2]

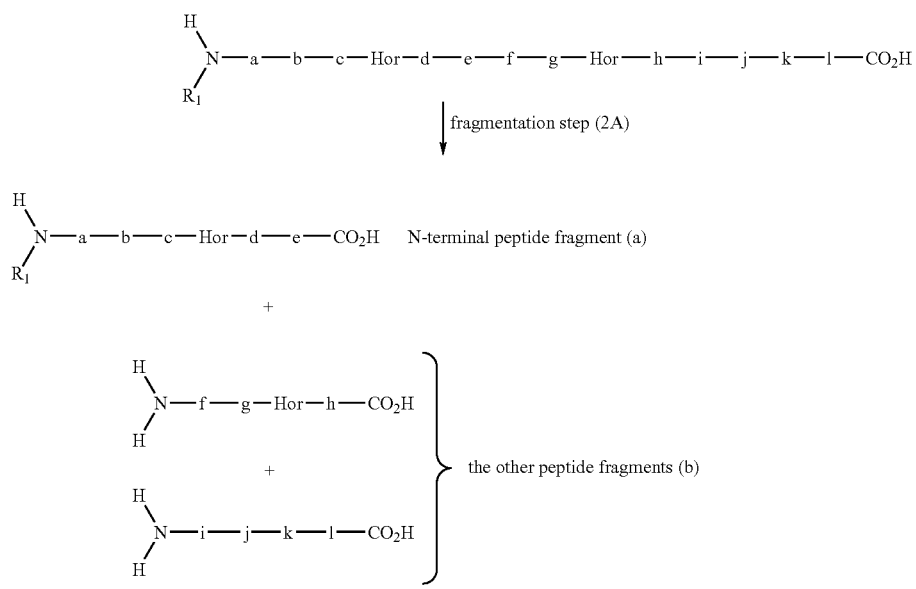

The scheme 2 shows an example in which an endoprotease cleaves on the C-terminal side of the residues e and h. As a result of fragmentation, the guanidinated protein is cleaved into a desired peptide fragment (a) that contains the modified N-terminus of the protein of interest, and the other peptide fragments (b) As shown by the scheme 2, each of the other peptide fragments (b) includes an unsubstituted amino group that has resulted from the hydrolysis of peptide bonds.

[Fragmentation Step (2A')]

This step may be carried out in a similar manner to the fragmentation step (2A): a protein of interest is subjected to chemical fragmentation or enzymatic digestion to generate an N-terminal peptide fragment (a') and the other peptide fragments (b'). As opposed to the fragmentation step (2A), the unguanidinated protein can be cleaved by any endoprotease, including Lys-C.

[Guanidination Step (1A')]

In a similar manner to the guanidination step (1A), each of the peptide fragments (a') and (b') obtained in the fragmentation step (2A') are then protected on the side chain-amino groups by guanidination. Guanidination occurs selectively on the side chain-amino groups, leaving the unsubstituted amino groups of the peptide fragments (a') and (b') unguanidinated. As a result, an N-terminal peptide fragment (a) and the other peptide fragments (b), each protected on the side chain-amino groups, are obtained. Theoretically, except for the case in which the enzyme used in the fragmentation step (2A') is Lys-C, the resulting peptide fragments will be identical to those obtained by the guanidination step (1A) and the fragmentation step (2A). In this description, all of the peptide fragments generated by the guanidination and the fragmentation, including those generated by the use of Lys-C, are collectively referred to as "N-terminal peptide (a)" and "the other peptide fragments (b)."

[Separation Step (3A)]

The desired peptide fragment (a) having the modified N-terminus is separated from the other amino group-containing peptide fragments (b) by taking advantage of the difference in the reactivity or the affinity to substrate: The other peptide fragments (b) are allowed to bind to substrate while the N-terminal peptide fragment (a) to be collected is eluted.

When the N-terminal peptide fragment (a) is separated from the other fragments (b) based on the difference in their reactivities with substrate, it is preferred that chemically the substrate includes molecules or part of molecules that react with the amino groups of the other fragments (b) to form covalent bonds. Such substrate may consist of a proper carrier, such as resin, with the aforementioned molecules immobilized onto the carrier, or it may consists of a carrier and a polymer of a monomer that includes the aforementioned molecules or part of the molecules, with the polymer being immobilized onto the carrier. Such a polymer alone may serve as the substrate. Those skilled in the art may properly determine the material and the shape of the carrier, as well as the shape of the polymer.

Examples of the substrate include p-phenylene diisothiocyanate (DITC) polymer resin, and allylamine polymer resin. These substrates consist of a resin with plural of DITC molecules or allylamime molecules immobilized thereon.

The following scheme 3 shows one example of this step in which a DITC polymer resin is used as the substrate. The DITC polymer resin is formed by immobilizing DITC onto a resin.

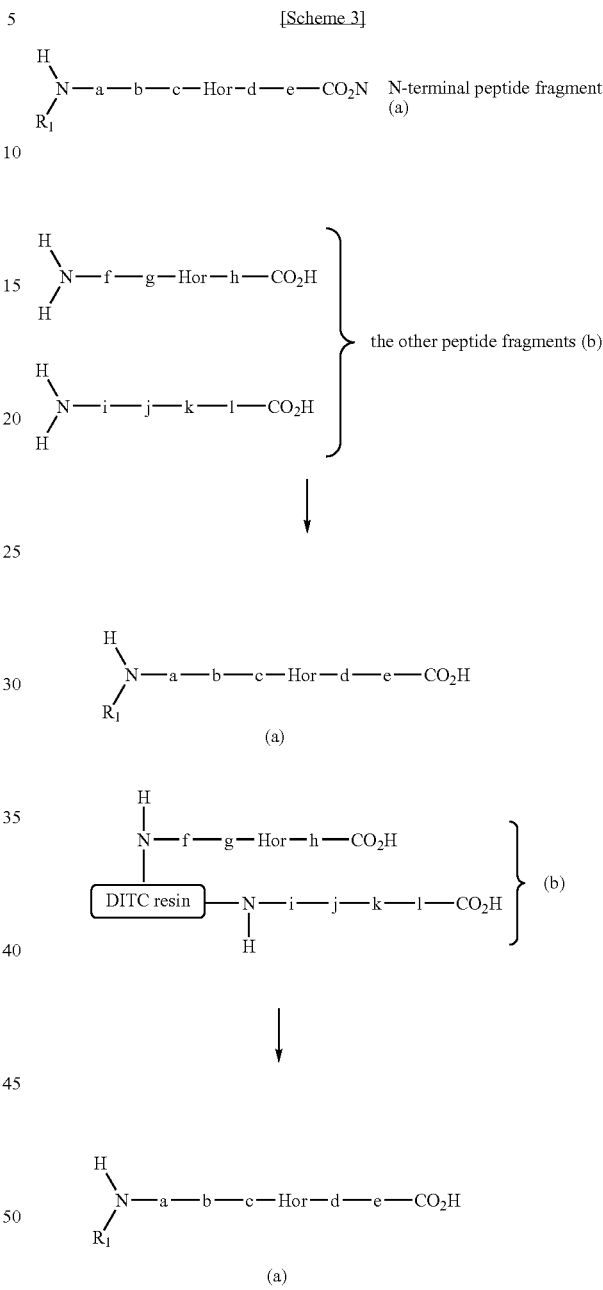

As shown by the scheme 3, the other peptide fragments (b), which contain amino groups, chemically react with DITC on the substrate to form covalent bonds whereas the desired peptide fragment (a), which has the modified N-terminal and does not have amino groups, remains unreacted with DITC and is thus eluted. In this manner, the peptide fragment containing the N-terminus of the protein of interest can be selectively collected.

As described above, the substrate used in this step binds to unsubstituted amino groups. Thus, in addition to the α-amino groups of the other peptide fragments, the substrate can also bind to the side chain-amino groups of the amino acid residues containing side chain-amino groups in the case that the side chain-amino groups are not properly protected. This is unfavorable since the N-terminal peptide fragments also bind to the substrate. For this reason, the protection is previously provided, for example, by the above-described guanidination.

When the N-terminal peptide fragment (a) is separated from the other fragments (b) based on the difference in their affinities to substrate, an affinity compound is coupled to the N-terminus of the other peptide fragments (b) after the fragmentation step (2A) and before the separation step (3A). As used herein, the term "affinity compound" refers to a compound that can specifically bind to a particular type of molecule or a particular part of the molecule to form a complex. In this case, a ligand consisting of the particular molecule or a ligand containing the particular part of the molecule is immobilized to serve as the substrate.

An example of combination of the affinity compound and the ligand is a combination of an antigen and its corresponding antibody. The term "antigen" as used herein refers to an agent that can bind to an antibody and encompasses small molecules such as hapten. Specific examples of the antigens include nitrophenol derivatives, lactosides, phenylazo derivatives and complexes thereof and specific examples of their corresponding antibodies include antibodies produced by using these antigens.

Another preferred combination of the affinity compound and the ligand is a biotin derivative and avidin.

In coupling the affinity compound, for example, in the case of coupling the carboxyl group of an antigen with the amino group of a peptide fragment, a crosslinking agent such as a water-soluble carbodiimide is used. Glutaraldehyde is preferably used as a crosslinking agent to couple the amino group of an antigen with the amino group of a peptide fragment. When it is desired to couple a biotin derivative with the amino group of a peptide fragment, a biotin activated ester is reacted with the peptide fragment.

One example of this step is shown by the following scheme 4, in which the affinity compound is denoted by a triangular symbol.

[Scheme 4]

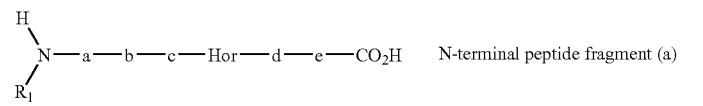

N-terminal peptide fragment (a)

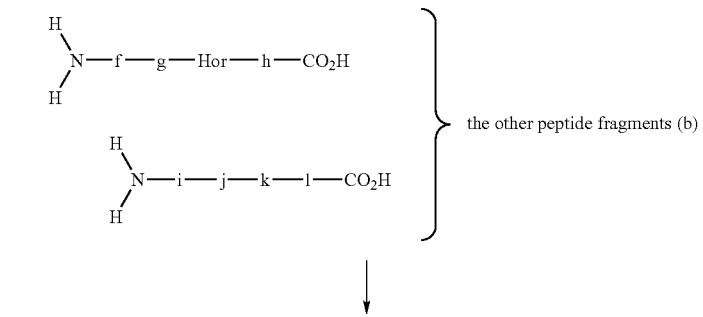

the other peptide fragments (b)

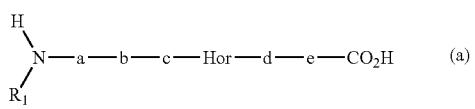

(a)

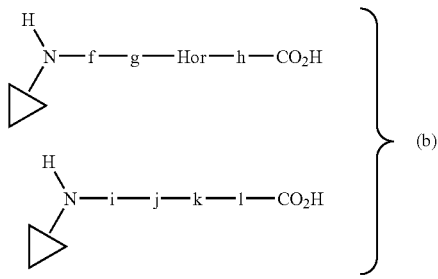

(b)

-continued

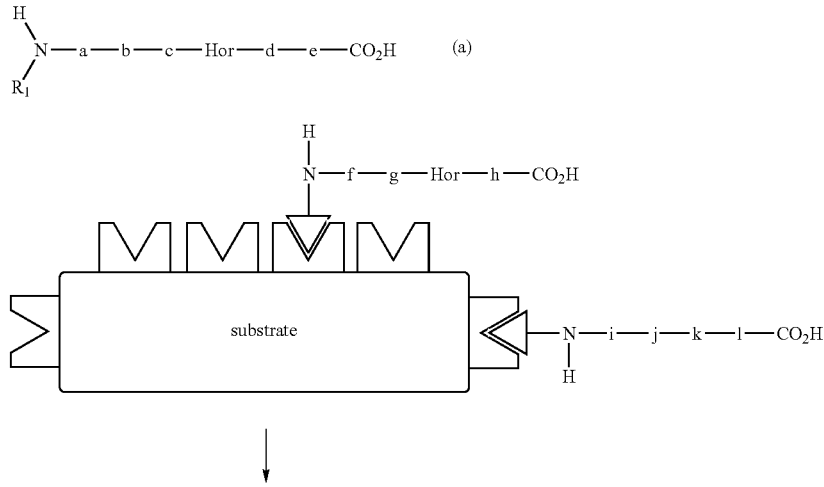

(a)

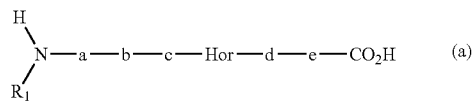

(a)

As shown by the scheme 4, the other peptide fragments (b) modified by coupling with the affinity compound bind to the ligand immobilized onto the substrate to form an antigen/antibody complex or a biotin/avidin complex. As a result, the desired peptide fragment (a) to be collected, which has the modified N-terminus, remains unbound and is thus eluted. In this manner, the peptide fragments containing the N-terminus of the protein of interest can be selectively collected.

Described next is the case in which the N-terminus of a protein of interest has not been modified. As shown in FIG. 1, when the protein of interest does not have a modified N-terminus, a guanidination step (1B) is first performed and subsequently the protein of interest is modified on the unmodified N-terminus. The process then proceeds either via a fragmentation step (2B) to a separation step (3B), or via a fragmentation step (2C) to a separation step (3C), depending on the type of the modification on the N-terminus. The following scheme 5 shows one example of the flow from the guanidination step (1B) to the fragmentation step (2B) or (2C). In the equation, $R_2$ represents a modification group of the unmodified N-terminus.

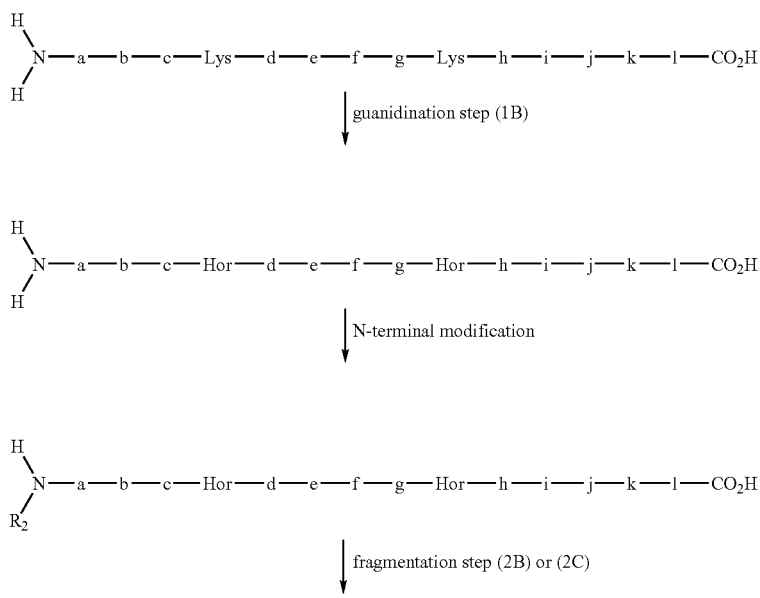

-continued

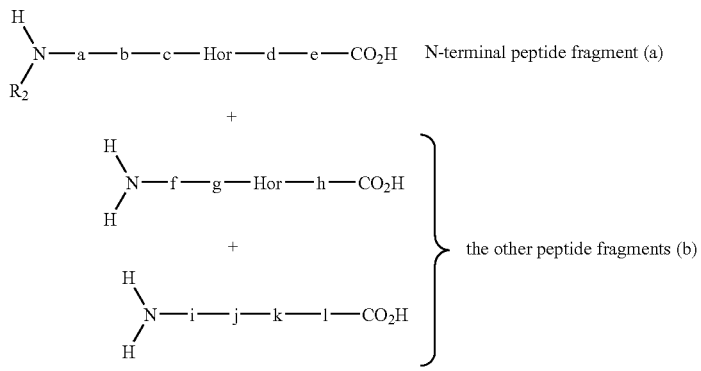

N-terminal peptide fragment (a)

the other peptide fragments (b)

[Guanidination Step (1B)]

In this step, the side chain-amino groups of amino acid residues containing side chain-amino goups are protected in a similar manner to the guanidination step (1A). One example of guanidination reagents suitable for use in the guanidination step (1B) is o-methylisourea. In this step, a guanidinated protein, in which the side chain-amino groups have been converted to guanidino groups, can be obtained.

[N-terminal Modification]

The resulting guanidinated protein is then modified on its unmodified N-terminus before subjected to fragmentation. Once modified, the N-terminal amino group is distinguished from the unsubstituted amino groups generated in the succeeding fragmentation of the protein.

The above-described affinity compounds may be used to modify the unmodified N-terminus. For example, the antigens and biotin derivatives may be used. A preferred antigen is one that is not susceptible to hydrolysis by enzymes and the like used in the subsequent fragmentation step (2B). One example is hapten. The affinity compound is coupled to the guanidinated protein to give a guanidinated protein with its N-terminus modified with the affinity compound (The process now proceeds to the fragmentation step (2B)).

Alternatively, the unmodified N-terminus may be modified with other suitable compounds other than the affinity compounds. Examples of such compounds include phenylisothiocyanate, fluorescein isothiocyanate. In this case, the addition of these compounds to the unmodified N-terminus of the guanidinated protein introduces a phenylthiocarbamoyl group and a fluorescein thiocarbamoyl group and the like. In this manner, a guanidinated protein with its N-terminus modified with a suitable substituent can be obtained (The process now proceeds to the fragmentation step (2C)).

The fragmentation and separation of the two differently modified proteins will now be described.

[Fragmentation Step (2B)]

First, a guanidinated protein that is modified on the N-terminus with the affinity compound is described.

Once modified on the unmodified N-terminus with the affinity compound, the guanidinated protein is cleaved, in the same manner as in the above-described fragmentation step (2A), into an N-terminal peptide fragment (a) modified with the affinity compound and the other peptide fragments (b) with unsubstituted amino groups.

[Separation Step (2B)]

The resulting peptide fragments (a) and (b) are separated based on the difference in the reactivity or affinity to substrate.

As described with regard to the separation step (3A), when the peptide fragments are separated based on the difference in the reactivity with substrate, DITC polymer resin or other materials that can chemically react with amino groups to form covalent bonds are preferably used as the substrate. Thus, as described with reference to the scheme 3, the other peptide fragments (b) with amino groups covalently bind to the substrate, whereas the desired N-terminal peptide fragment (a) with the introduced affinity compound to be collected remains unbound and is thus eluted. In this manner, the peptide fragments containing the N-terminus of the protein can be selectively collected.

As described with regard to the separation step (3A), when the peptide fragments are separated based on the difference in the affinity to substrate, it is preferred that the substrate consists of a carrier with a ligand that can form a complex with the affinity compound and is immobilized onto the carrier. For example, an antibody is selected to serve as the ligand when the N-terminus is modified with an antigen, and avidin is selected to serve as the ligand when the N-terminus is modified with a biotin derivative. Shown with reference to the scheme 6 below is an example of the carrier onto which a ligand has been immobilized.

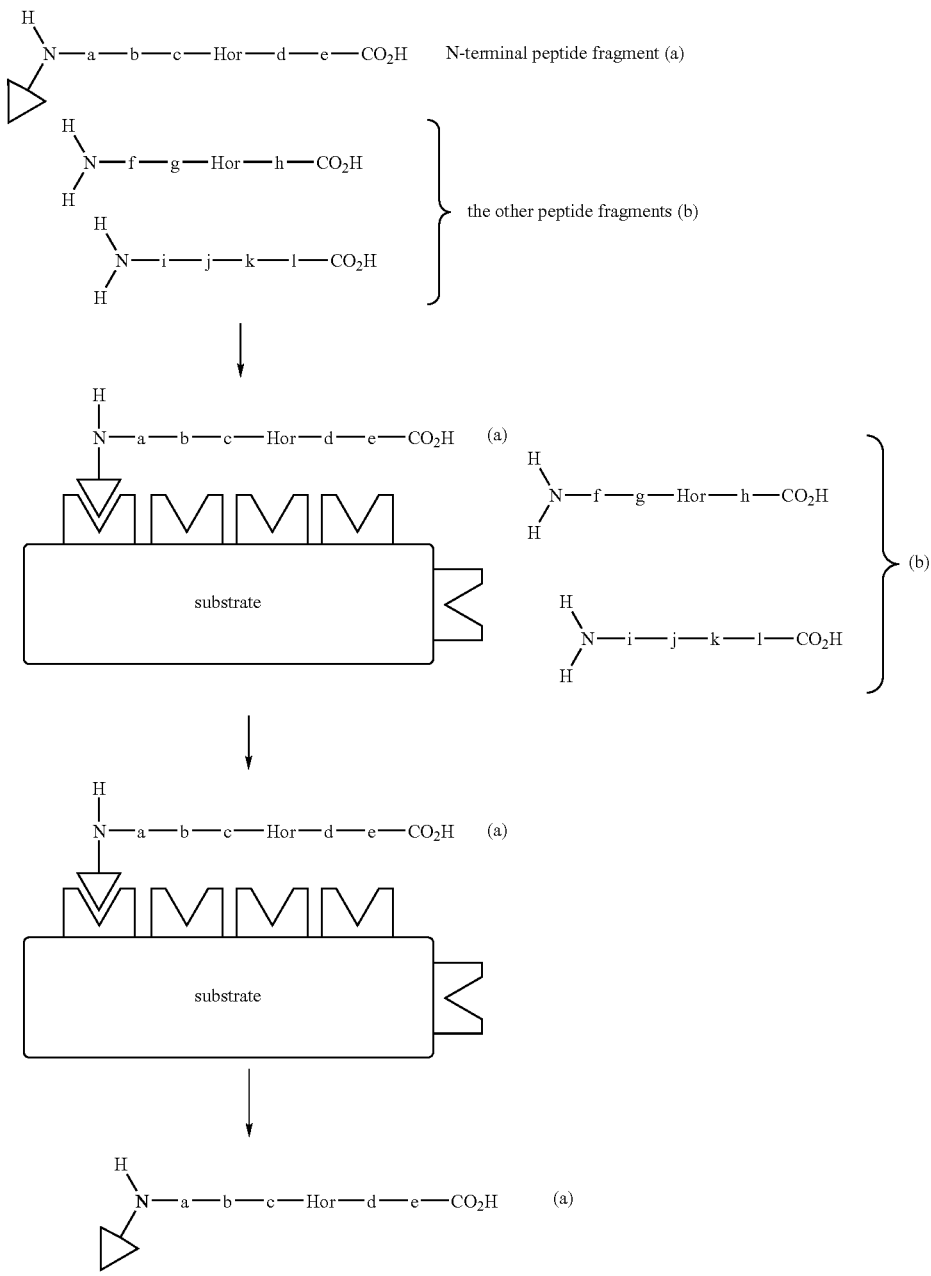

[Scheme 6]

First, the N-terminal peptide fragment (a) with the introduced affinity compound to be collected specifically binds to the ligand immobilized onto the substrate, whereas the other peptide fragments (b) with unsubstituted amino groups remain unbound and are thus eluted. Subsequently, the substrate with the bound N-terminal peptide fragment (a) is thoroughly washed to decrease the binding force between the antigen and the antibody and to thus cause the desired N-terminal peptide fragment to elute. In this manner, the peptide fragments containing the N-terminus of a protein can be selectively collected.

The binding force between the antigen and the antibody may be weakened for example by shifting the pH to acidic or by increasing the salt concentration.

The binding force between biotin and avidin may be weakened for example by oxidation with hydrogen peroxide, treatment with guanidine hydrochloride, and temperature increase in organic solvent such as acetonitrile.

[Fragmentation Step (2C)]

Next, fragmentation of a guanidinated protein in which the N-terminus has been modified with a proper substituent other than the affinity compound is described.

Once modified on the unmodified N-terminus with a proper substituent other than the affinity compound, the guanidinated protein is cleaved, in the same manner as in the above-described fragmentation step (2A), into a modified N-terminal peptide fragment (a) to be collected and the other peptide fragments (b) with amino groups.

[Separation Step (2C)]

The resulting peptide fragments (a) and (b) are separated based on the difference in the reactivity or affinity to substrate.

As described with regard to the separation steps (3A) and (3B), when the peptide fragments are separated based on the difference in the reactivity with substrate, DITC polymer resin or other materials that can react with amino groups to form covalent bonds are preferably used as the substrate. Thus, as described with reference to the scheme 3, the other peptide fragments (b) with amino groups covalently bind to the substrate, whereas the desired N-terminal peptide fragment (a) with the introduced affinity compound remains unbound and is thus eluted. In this manner, the peptide fragments containing the N-terminus of the protein can be selectively collected.

When the N-terminal peptide fragment (a) is separated from the other fragments (b) based on the difference in their affinities to substrate, an affinity compound is coupled to the N-terminus of the other peptide fragments after the fragmentation step (2C) and before the separation step (3C). In this case, as described in the separation step (3A), a compound that can specifically bind to the affinity compound to form a complex is immobilized and used as the substrate. Among preferred combinations of the affinity compound and the ligand are a combination of an antigen and its antibody and a combination of a biotin derivative and avidin as described above. As shown by the scheme 4 above, the other peptide fragments (b) coupled with the affinity compound bind to the ligand immobilized on the substrate to form antigen/antibody complexes and biotin/avidin complexes. As a result, the desired peptide fragment (a) containing the N-terminus to be collected remains unbound and thus eluted. In this manner, the peptide fragments containing the N-terminus of the protein of interest can be selectively collected.

In the manner described above, the N-terminal-containing fragments (a) can be selectively collected whether or not the protein of interest is modified on the N-terminus. Once collected, the N-terminal peptide fragments (a) may be subjected to MS/MS or other proper analyses.

The other peptide fragments (b) on the other hand may be collected and analyzed as follows: in the case as shown in the scheme 6, the solution used to wash the substrate is collected since the other peptide fragments (b) elute first in such a case. In the case as shown in the scheme 4, in which the other peptide fragments (b) form antigen/antibody complexes or biotin/avidin complexes and remain bound to the substrate, the binding between the peptide fragments (b) and the substrate is weakened in the above-described manner so that the peptide fragments (b) can be collected. Once collected, the mixture of the other peptide fragments (b) may be subjected to PMF, MS/MS or other proper analyses.

In this manner, the amino acid sequence of a protein can be determined from the N-terminus.

EXAMPLES

Figure 2:
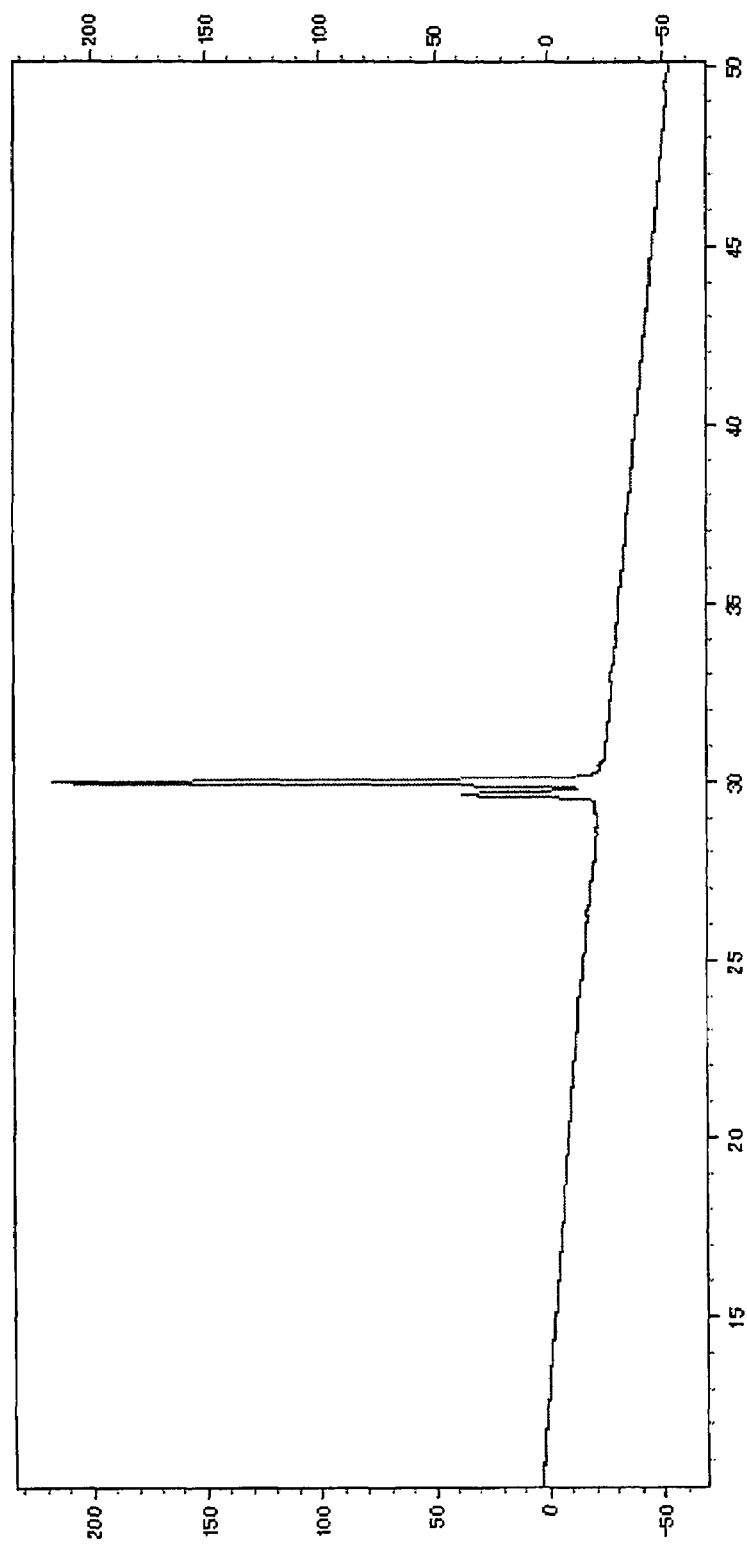
FIG. 2 is an HPLC chromatogram of guanidinated neurotensin obtained in Example 1.

The present invention will now be described in further detail with reference to Examples, which are provided by way of example only and are not intended to limit the scope of the invention in any way. In the following, "%" refers to % by weight unless specifically mentioned. Further, in HPLC chromatogram of FIG. 2 to FIG. 4, the horizontal axis shows time (min) and the virtual axis shows intensity of the peak, and in MALDI spectrum of FIG. 5 to FIG. 10, the horizontal axis shows Mass/Charge and the virtual axis shows intensity (% Int.) of the ion peak.

Example 1

In this example, N-terminal peptide fragment is collected in a series of steps of guanidination step (1A), fragmentation step (2A), and separation step (3A).

In this example, neurotensin was used as a sample. While neurotensin is a peptide obtained from humans, bovines, and canines, an artificial neurotensin (Pyr-Leu-Tyr-Glu-Asn-Lys-Pro-Arg-Arg-Pro-Tyr-Ile-Leu (SEQ ID NO: 1 in sequence listing), Peptide Institute Inc.) was used in the present examples. This peptide has pyroglutamic acid residue represented as Pyr at its N-terminus.

(Guanidination Step (1A))

30 μl 0.67 mM neurotensin, a 33 μl 9N aqueous ammonia solution, and 9 μl 6M o-methylisourea are mixed with one another and the reaction was allowed to proceed at 65° C. for 30 min to guanidinated the peptide. A reversed-phase HPLC chromatogram of the guanidinated neurotensin was shown in FIG. 2 (2 nmol), in which the main peak observed after approximately a 30-minute elution time was determined to be the guanidinated neurotensin and the minor peak appearing immediately before the main peak was determined to be unreacted neurotensin by MALDI.

(Fragmentation Step (2A))

Figure 3:
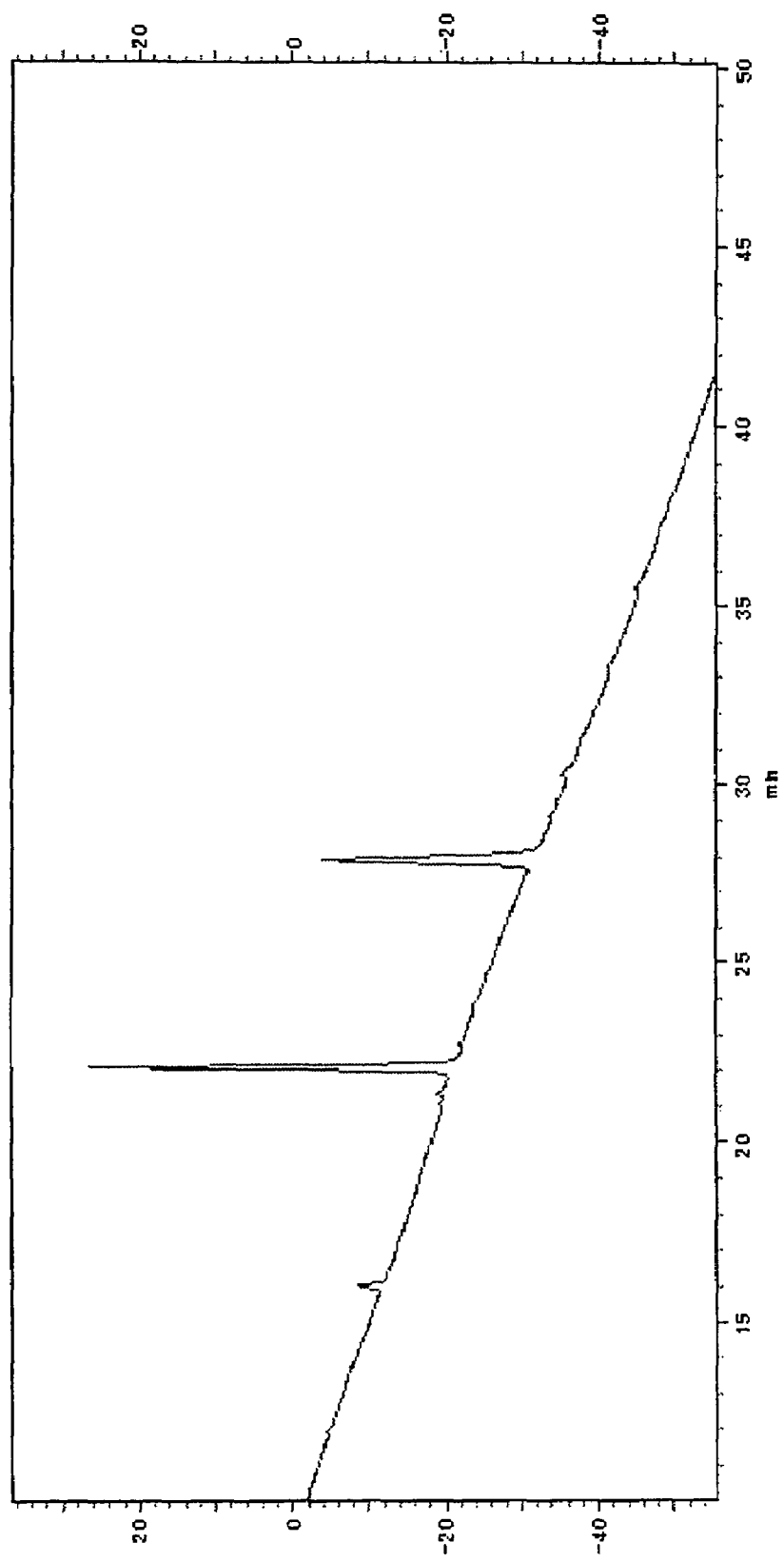
FIG. 3 is an HPLC chromatogram of trypsin digests of the peptide fragment obtained in Example 1.
Figure 5:
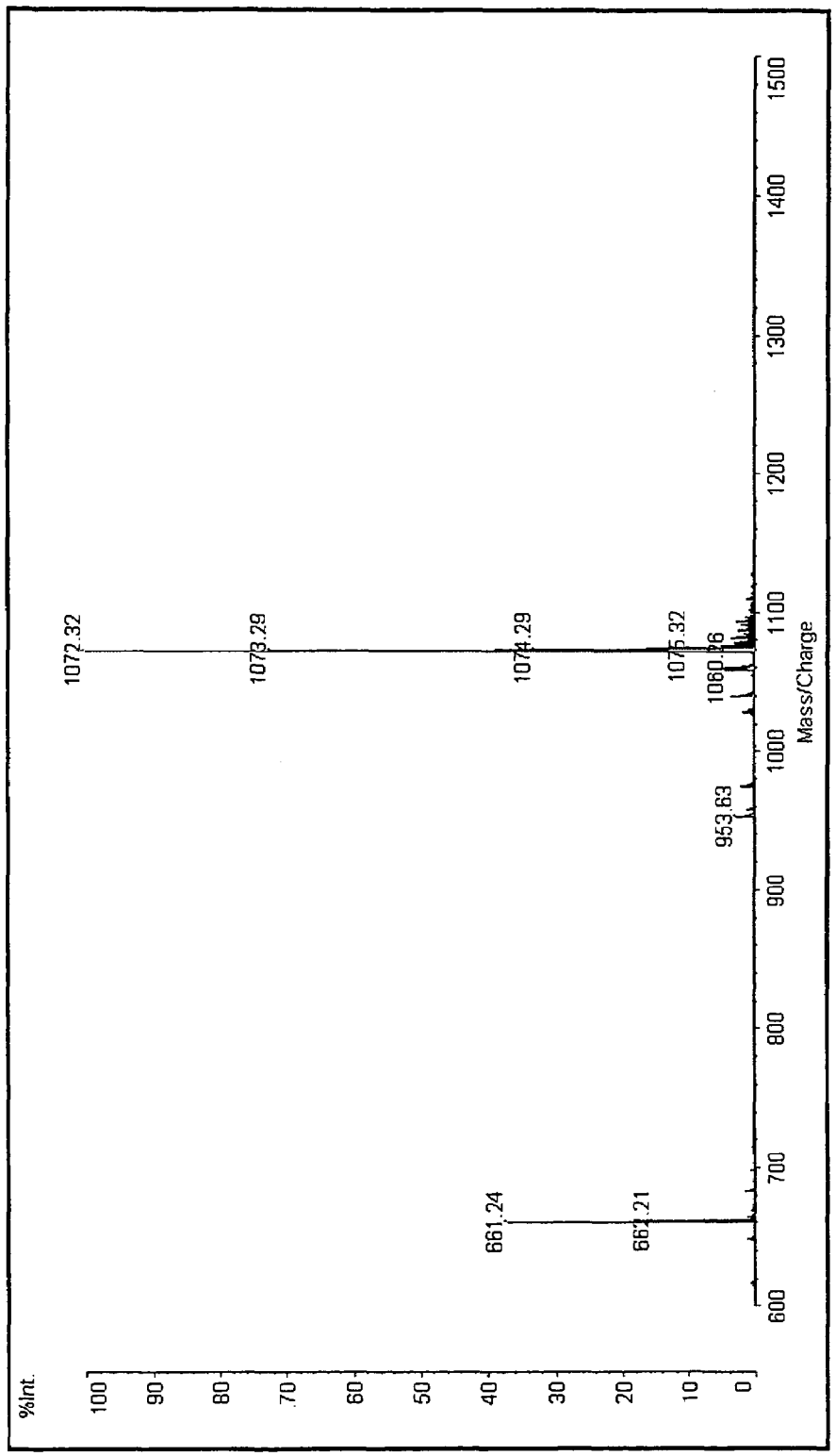
FIG. 5 is a MALDI spectrum of the trypsin digests of the peptide fragment obtained in Example 1.

The main peak fraction was collected and was purified by reverse-phased HPLC. The purified product was dried to form a solid sample. To the sample, a 30 μl trypsin solution (0.1 μg/μl), prepared by adding trypsin to a 5 mM aqueous solution of calcium chloride and 50 mM ammonium bicarbonate was added. The mixture was left overnight to digest the guanidinated peptide. A reverse-phase HPLC chromatogram and MALDI spectra of the digested sample are shown in FIGS. 3 and 5, respectively. The two peaks observed in FIG. 3 are [M+H]$^+$ molecular ion peaks corresponding to Pyr-Leu-Tyr-Glu-Asn-Lys-Pro-Arg (SEQ ID NO:2 in sequence listing; 1072 (m/z)) having pyroglutamic acid residue represented as Pyr at its N-terminus, and Arg-Pro-Tyr-Ile-Leu (SEQ ID NO: 3; 661 (m/z)), each detected in FIG. 5.

(Separation Step (3A))

3.3 μl of the digested sample, 32.7 μl 100 mM Tris-HCl buffer (pH 8.3), 4 μl 12.5% aqueous solution of trimethylamine, and 4 μl acetonitrile are mixed with one another. The mixture was loaded on a DITC polymer resin column (CTFF-1 column (P/N 292–02400), Shimazu Corporation) and the reaction was allowed to proceed at 60° C. for 1 hour. After the reaction, the resin was washed with 300 μl of a mixture of 0.1% trifluoroacetic acid, 2-propanol, and acetonitrile containing the respective components at a volume ratio of 4:3:3. The resulting eluate was collected and was dried to form a solid product. The product was then redissolved in a 0.1% aqueous solution of trifluoroacetic acid and was subjected to analysis by reverse-phase HPLC and MALDI.

Figure 4:
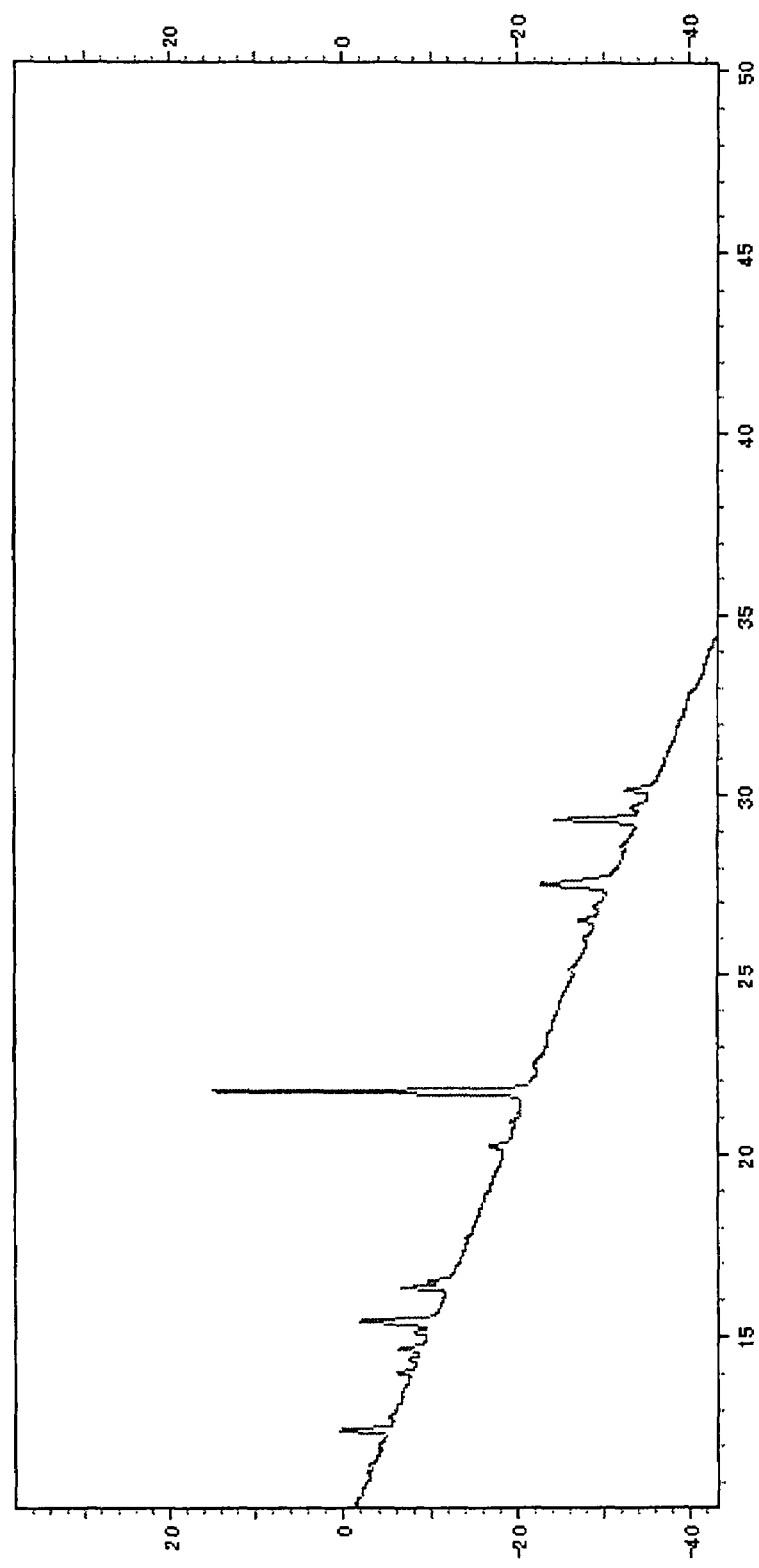
FIG. 4 is an HPLC chromatogram of the eluted fraction by separation on a DITC polymer resin column, obtained in Example 1.
Figure 6:
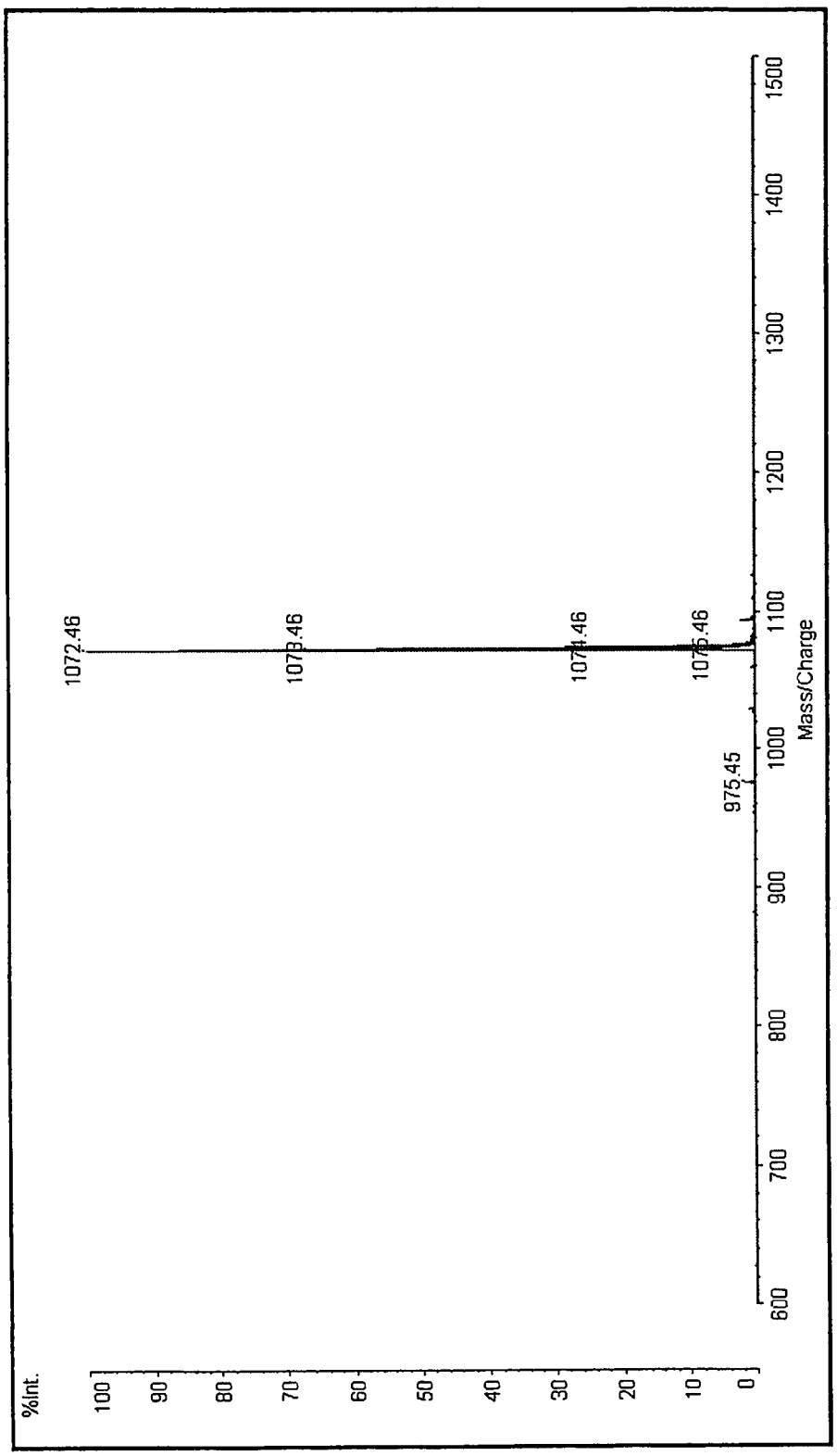
FIG. 6 is a MALDI spectrum of the eluted fraction by separation on a DITC polymer resin column, obtained in Example 1.

The reverse-phase HPLC chromatogram and MALDI spectra of the product are shown in FIGS. 4 and 6, respectively. Of the two peaks detected in FIG. 3, the peak appearing after 22 minutes was only seen in FIG. 4. This, taken together with the results of FIG. 6, suggests that the detected [M+H]$^+$ peak corresponds to Pyr-Leu-Tyr-Glu-Asn-Lys-Pro-Arg (SEQ ID NO:2 in sequence listing; 1072 (m/z)). Accordingly, it has been proven that the N-terminal peptide fragment of neurotensin was selectively collected.

Example 2

In this example, N-terminal peptide fragment is collected in a series of steps of guanidination step (1B), N-terminal modification step, fragmentation step (2B), and separation step (3B).

In this example, Lysozyme (EC 3.2.1.17 from Chicken Egg White: SIGMA Chemical Company) was used as a sample. Lysozyme is dissolved in distilled water with a concentration of 100 pmol/μl. 10 μl of the resulting dissolved Lysozyme was dropped to PVDF membrane (Polyvinylidene difluoride membrane: Nippon Genetics Co., Ltd.), which was cut to a circular with 8 mm in diameter, and dried to be obtained sample-applied PVDF membrane.

(Reduction-alkylation)

The sample applied PVDF membrane was put into a 1.5 ml tube. 1 ml mixture of 10 mM dithiothreitol in 100 mM ammonium bicarbonate solution and acetonitrile (8:2 v/v) was added to the tube and reacted at 56° C. for 1 hour. After the reaction, the added mixture was removed from the tube. 1 ml mixture of 55 mM iodoacetamide in 100 mM ammonium bicarbonate solution and acetonitrile (8:2 v/v) was added to the tube and reacted at room temperature for 45 minutes. After the reaction, the PVDF membrane was removed from the tube, put into a beaker with 100 ml distilled water, and stirred for 10 minutes to be washed. After the wash, the PVDF membrane was dried.

(Guanidination Step (1B))

The resulting PVDF membrane reduction-alkylation treated was put into a new 1.5 ml tube. 1 ml mixture of 0.85M O-methylisourea hemisulfate in 7N aqueous ammonia and acetonitrile (8:2 v/v) was added to the tube and reacted at 60° C. for 30 minutes. The resulting PVDF membrane is removed from the tube, put into a beaker with 100 ml distilled water, and stirred for 10 minutes to be washed. After the wash, the PVDF membrane was dried.

(N-terminal Modification Step)

1) Synthesis of Biotinylcysteic Acid 3.4 mg sulfosuccinimide dissolved to 20 μl distilled water, 1.1 mg cysteic acid dissolved to 15 μl distilled water, and 1.65 μl triethylamine were mixed to react at 60° C. for 30 minutes. The product was purified by reverse phase HPLC, and the aimed biotinylcysteic acid was identified by MALDI-TOF MS. The structural formula of the biotinylcysteic acid obtained was shown below as formula (I).

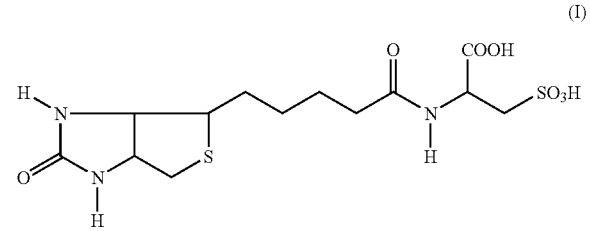

(I)

2) Coupling with N-terminus

The resulting PVDF membrane guanidination treated was put into a new 1.5 ml tube. 900 μl mixture of 2 mM biotinylcysteic acid (I) above obtained, 2 mM EDC (1-ethyl-3-(3-dimethyl aminopropyl)carbodiimide) and 5 mM Sulfo-NHS (N-hydroxysulfo succinimide) in 0.1 MES (2-(N-morpholino) ethanesulfonic acid) buffer, and acetonitrile (8:2 v/v) was added to the tube and react at 65° C. for 1 hour. After the reaction, the resulting PVDF membrane was removed from the tube, put into a beaker with 100 ml distilled water, and stirred for 10 minutes to be washed. After the wash, the PVDF membrane was dried.

(Fragmentation Step (2B))

The resulting PVDF membrane modification treated was put into a new 1.5 ml tube for digestion. 100 μl mixture of a mixed solution of 20 μg trypsin in 100 mM ammonium bicarbonate and 5 mM calcium chloride solution, and acetonitrile (8:2 v/v) was added to the tube for digestion, and digested at 36° C. overnight.

(Extraction of Digested Peptides from PVDF Membrane)

After the digestion, the liquid part was removed from the tube for digestion to be recovered to a new 1.5 ml tube for recovery. To the PVDF membrane remained in the tube for digestion was added 150 μl mixture of 0.1% aqueous TFA (trifluoroacetic acid) and acetonitrile (4:6 v/v), allowed to stand at 60° C. for 1 hour, and stirred to extract digested peptides from the PVDF membrane. The resulting extract solution was recovered to the above mentioned tube for recovery. A series of procedures of extraction of the digested peptides and recovery of the extract solution was done another two times. The obtained recovery was centrifuged to be dried up. The resulting dried digested peptides were used for "2) collecting N-terminal peptide fragment" in the separation step (3B) described below.

(Separation Step (3B))

1) Preparation of Avidin Resin

30 μl avidin resin (SoftLink™ SoftLease Avidin Resin: Promega) was put into a new 1.5 ml tube. 500 μl 0.1M phosphate buffer was added to the tube, stirred, centrifuged to be settled, and removed the supernatant. A series of procedures of adding phophate buffer, stirring, centrifuging and removing supernant was done another 2 times to equilibrate the avidin resin. To the resulting avidin resin was added 100 μl 5 mM biotinylcysteic acid (I) in 0.1M phosphate buffer and stirred for 30 minutes, to allow the avidin resin to absorb the biotinylcysteic acid. After the absorbance, the supernatant was removed. 500 μl 10% aqueous acetic acid was added to the resulting resin and stirred to extract biotinylcysteic acid from the avidin resin, and then, the resin was settled and the supernatant was removed. A series of procedures from adding the aqueous acetic acid to removing the supernatant was done another two times. This treatment was operated to prevented the avidin resin from nonspecifically absorb the N-terminal peptide fragment having modifying group by biotinylcysteic acid. The resulting avidin resin was equilibrated in the same manner as described above, to be used as a prepared avidin resin.

2) Collecting N-terminal Peptide Fragment

Figure 7:
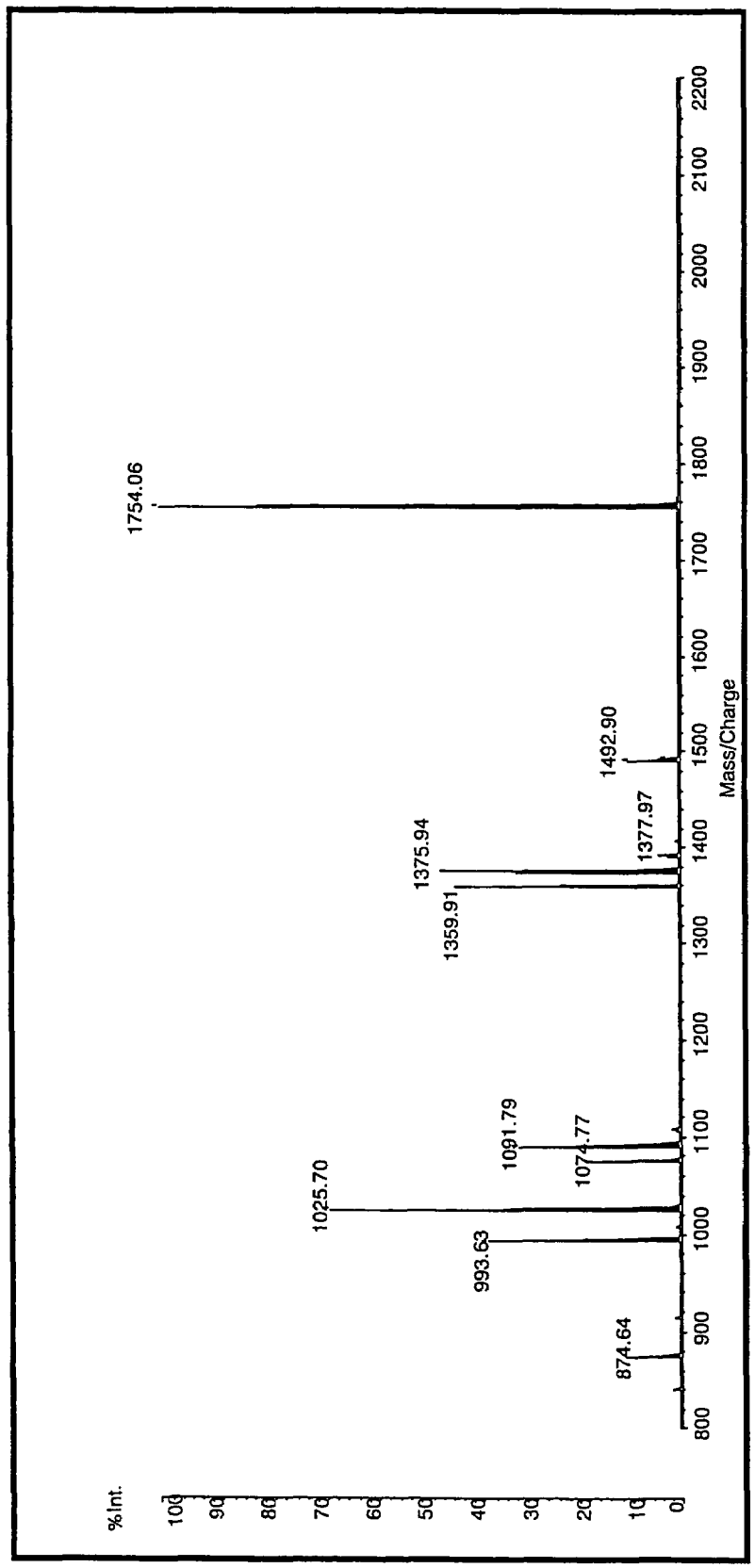
FIG. 7 is a MALDI spectrum of the trypsin digests of the peptide fragment obtained in Example 2.

The dried digested peptides obtained above was redissolved to 100 μl 0.1 mM phosphate buffer. 2 μl of the resulting redissolved digested peptides was desalted by using ZipTip™C18 (MILLIPORE) and subjected to analysis by MALDI. MALDI spectrum of thus obtained product is shown in FIG. 7, in which the peak detected at 1025.70 (m/z) corresponds to the N-termianl peptide fragment (Bio-cys-Hor-Val-Phe-Gly-Arg; SEQ ID NO:4; calcd. 1025.47 (m/z)) having modifying group by biotinylcysteic acid (represented as Bio-cys) and guanidinated lysine residue (represented as Hor). Along with this peak of the N-terminal peptide fragment, many of peaks corresponding to the other peptide fragments trypsin digested are also detected.

Figure 8:
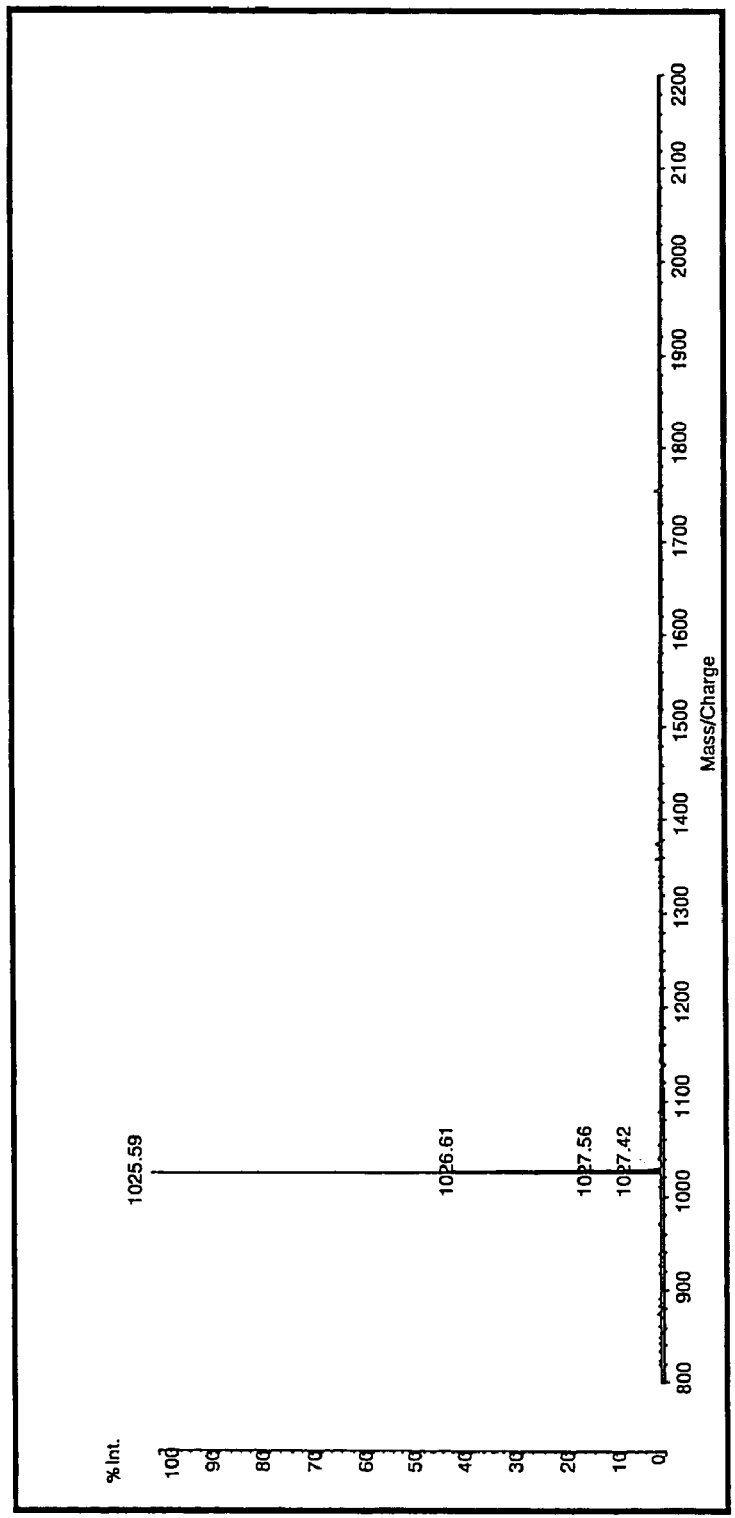
FIG. 8 is a MALDI spectrum of the absorbed fraction by separation on an avidin resin, obtained in Example 2.

Another 10 µl of the resulting redissolved digested peptides was applied to the prepared avidin resin obtained above, and stirred at room temperature for 1 hour to allow the avidin resin to absorb the N-terminal peptide fragment (having modifying group by biotinylcysteic acid). After the absorbance, the avidin resin was washed three times by using 500 µl 0.1 mM phosphate buffer to remove the other peptide than the N-terminal peptide fragment from the avidin resin. Through the avidin resin was flowed 150 µl 10% aqueous acetic acid twice and 150 µl mixture of 10% aqueous acetic acid and acetonitrile (1:1 v/v) once to elute the absorbed N-terminal peptide fragment off. Eluted N-terminal fragment was centrifuged to be dried up. The resulting dried N-terminal peptide fragment was redissolved to 10 µl 0.1% aqueous TFA and desalted by using ZipTip™C18 (MILLIPORE) and subjected to analysis by MALDI. MALDI spectrum of thus obtained product is shown in FIG. 8, in which the peak corresponding to the N-terminal peptide fragment seen in FIG. 7 is specifically detected at 1025.59 (m/z). Accordingly, it has been proven that the N-terminal peptide fragment was selectively collected.

Example 3

In this example, N-terminal peptide fragment is collected in a series of steps of fragmentation step (2A'), guanidination step (1A'), and separation step (3A).

In this example, ovalbumin (SIGMA) was used as a sample. ovalbumin is dissolved in distilled water with a concentration of 100 pmol/µl. 10 µl of the resulting dissolved ovalbumin was dropped to PVDF membrane (Polyvinylidene difluoride membrane: Nippon Genetics Co., Ltd.), which was cut to a circular with 8 mm in diameter, and dried to be obtained sample-applied PVDF membrane.

(Reduction-alkylation)

The sample applied PVDF membrane was put into a 1.5 ml tube. 1 ml mixture of 10 mM dithiothreitol in 100 mM ammonium bicarbonate solution and acetonitrile (8:2 v/v) was added to the tube and reacted at 56° C. for 1 hour. After the reaction, the added mixture was removed from the tube. 1 ml mixture of 55 mM iodoacetamide in 100 mM ammonium bicarbonate solution and acetonitrile (8:2 v/v) was added to the tube and reacted at room temperature for 45 minutes. After the reaction, the PVDF membrane was removed from the tube, put into a beaker with 100 ml distilled water, and stirred for 10 minutes to be washed. After the wash, the PVDF membrane was dried.

(fragmentation Step (2A'))

The resulting PVDF membrane was put into a new 1.5 ml tube for digestion. 100 µl mixture of a mixed solution of 20 µg trypsin in 100 mM ammonium bicarbonate and 5 mM calcium chloride solution, and acetonitrile (8:2 v/v) was added to the tube for digestion, and digested at 36° C. overnight.

(Extraction of Digested Peptides From PVDF Membrane)

After the digestion, the liquid part was removed from the tube for digestion to be recovered to a new 1.5 ml tube for recovery. To the PVDF membrane remained in the tube for digestion was added 150 µl mixture of 0.1% aqueous TFA (trifluoroacetic acid) and acetonitrile (4:6 v/v), allowed to stand at 60° C. for 1 hour, and stirred to extract digested peptides from the PVDF membrane. The resulting extract solution was recovered to the above mentioned tube for recovery. A series of procedures of extraction of the digested peptides and recovery of the extract solution was done another two times. The obtained recovery was centrifuged to be dried up.

(Guanidination Step (1A'))

The resulting dried digested peptides was put into a new 1.5 ml tube for guanidination. 7 µl 0.85M O-methylisourea hemisulfate in 7N aqueous ammonia was added to the tube and reacted at 60° C. for 30 minutes. 10 µl 10% aqueous TFA was additionally added to the tube to quench the reaction and the resulting reaction solution was centrifuged to be dried up. The resulting dried peptide was provided for the following separation step (3A).

(Separation Step (3A))

Figure 9:
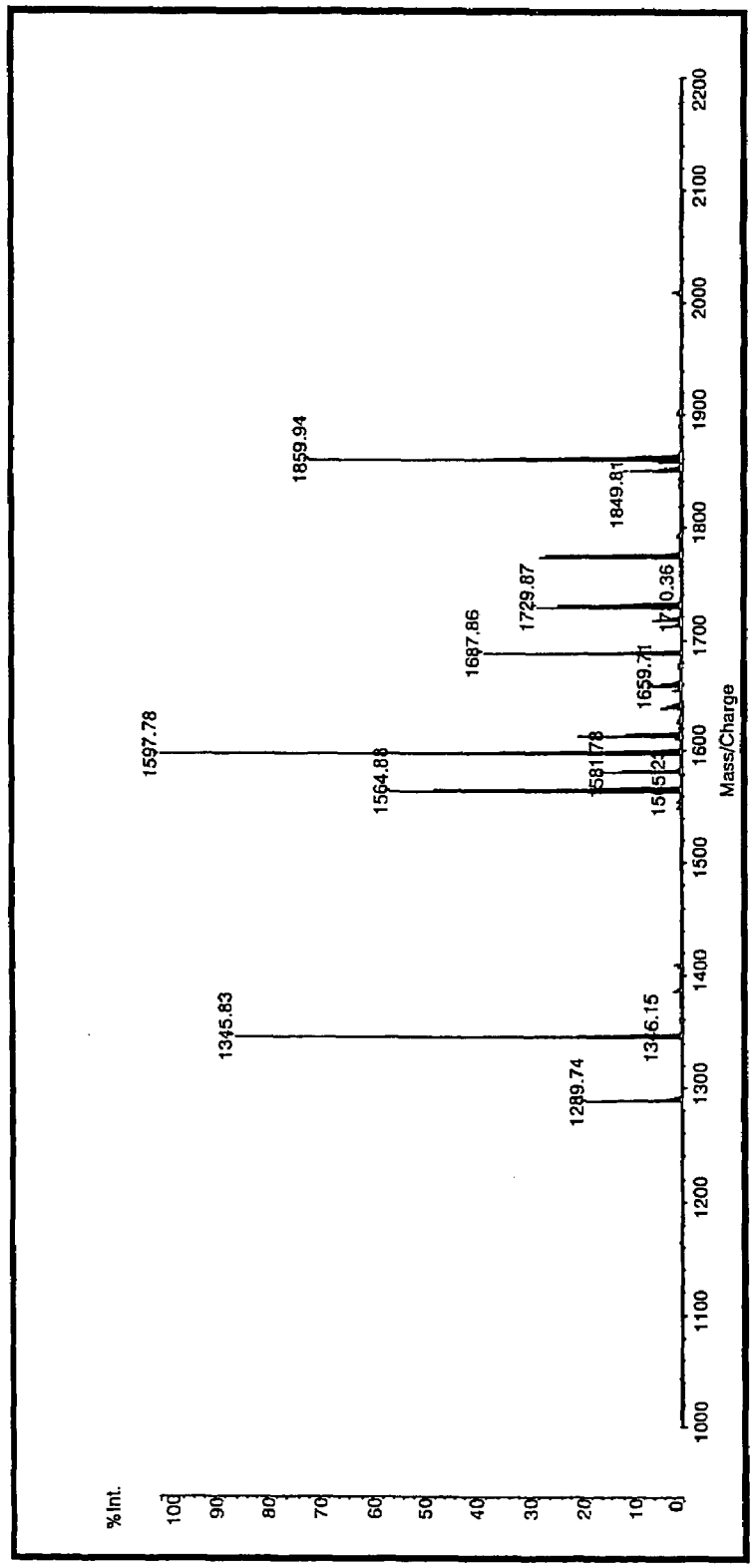
FIG. 9 is a MALDI spectrum of the trypsin digests of the peptide fragment obtained in Example 3.

3 mg DITC-Glass (Isothiocyanate glass: SIGMA) was put into a 500 µl tube. On the other hand, the above dried peptide which had obtained by digestion and guanidination was dissolved to 7 µl distilled water. A part of the resulting dissolved peptide digested and guanidinated was subjected to analysis by MALDI. MALDI spectrum of thus obtained product is shown in FIG. 9, in which the peak detected at 1849.81 (m/z) corresponds to the N-termianl peptide fragment (Ac-Gly-Ser-Ile-Gly-Ala-Ala-Ser-Met-Glu-Phe-Cys (Cam)-Phe-Asp-Val-Phe-Hor; SEQ ID NO: 5; calcd. 1849.83 (m/z)) having acetylated N-terminal glycine residue (represented as Ac-Gly) and carbamoylmethylated cystein residue (represented as Cys (Cam)). Along with this peak of the N-termianl peptide fragment, many of peaks corresponding to the other peptide fragments are also detected.

Figure 10:
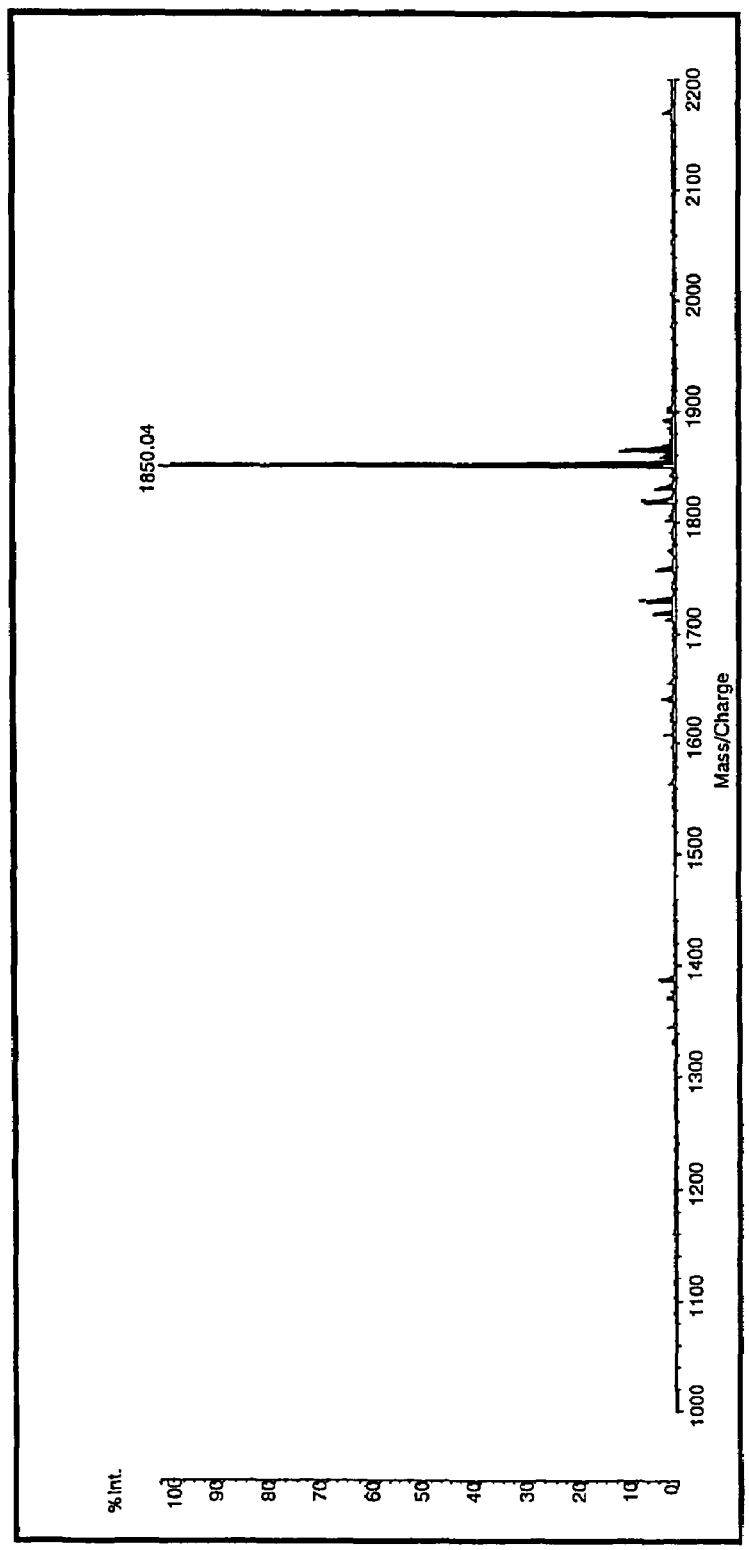
FIG. 10 is a MALDI spectrum of the eluted fraction by separation on DITC-glass, obtained in Example 3.

7 µl 12% aqueous triethylamine was added to the remainder of the above dissolved peptide digested and guanidinated, and was applied to the above DITC-Glass to react by standing at 60° C. for 2 hour and then shaking for 1 hour. After reaction, 100 µl mixture of 0.1% aqueous TFA, acetonitrile and isopropanol (42:18:40 (v/v/v)) was added, stirred, settled the DITC-Glass and recovered the supernatant to the tube for recovery. A series of the procedure from adding the mixture to recovering the supernatant was done another two times. The resulting recovery in the tube was centrifuged to be dried up. The resulting dried peptide was redissloved to 10 µl 0.1% aqueous TFA and desalted by using ZipTip™C18 (MILLIPORE) and subjected to analysis by MALDI. MALDI spectrum of thus obtained product is shown in FIG. 10, in which the peak corresponding to the N-terminal peptide fragment seen in FIG. 9 is specifically detected at 1850.04 (m/z). Accordingly, it has been proven that the N-terminal peptide fragment was selectively collected.

The above-described Examples shows concrete three modes within the scope of the present invention, however, the present invention can be carried out in various other modes. Therefore, the above-described Examples are merely illustrative in all respects, and must not be construed as being restrictive. Further, the changes that fall within the equivalents of the claims are all within the scope of the present invention.

What is claimed is:

1. A method for selectively collecting the N-terminal peptide fragment of a protein, comprising:
   a protection step (1) of protecting side chain-amino groups of amino acid residues containing side chain-amino groups of a protein of interest to obtain a protected protein protected on the side chain-amino groups;
   a fragmentation step (2) of cleaving the protected protein into one N-terminal peptide fragment (a) containing the N-terminus of the peptide of interest and one or more of peptide fragments (b) other than the N-terminal peptide fragment (a); and
   a separation step (3) of separating the N-terminal peptide fragment (a) from the other peptide fragments (b) by selectively eluting the N-terminal peptide fragment (a) based on the difference in their reactivity or affinity to substrate, wherein the selective elution is achieved by allowing the N-terminal peptide fragment (a) to bind to the substrate while allowing the other peptide fragments (b) to elute and subsequently eluting the bound N-terminal peptide fragment (a).

2. A method for selectively collecting the N-terminal peptide fragment of a protein, comprising:
   a fragmentation step (2') of cleaving a protein of interest into one N-terminal peptide fragment (a') and one or more of peptide fragments (b') other than the N-terminal peptide fragment (a');
   a protection step (1') of protecting side chain-amino groups of amino acid residues containing side chain-amino group of the N-terminal peptide fragment (a') and the other peptide fragments (b') to obtain a protected N-terminal peptide fragment (a) protected on the side chain-amino groups, along with the other protected polypeptide fragments (b) protected on the side chain-amino groups; and
   a separation step (3) of separating the N-terminal peptide fragment (a) from the other peptide fragments (b) by selectively eluting the N-terminal peptide fragment (a) based on the difference in their reactivity or affinity to substrate, wherein the selective elution is achieved by allowing the N-terminal peptide fragment (a) to bind to the substrate while allowing the other peptide fragments (b) to elute and subsequently eluting the bound N-terminal peptide fragment (a).

3. A method for selectively collecting the N-terminal peptide fragment of a protein, comprising:
   a protection step (1) of protecting side chain-amino groups of amino acid residues containing side chain-amino groups of a protein of interest modified on the N-terminus to obtain a protected protein protected on the side chain-amino groups;
   a fragmentation step (2) of cleaving the protected protein into one N-terminal peptide fragment (a) containing the N-terminus of the peptide of interest and one or more of peptide fragments (b) other than the N-terminal peptide fragment (a); and
   a separation step (3) of separating the N-terminal peptide fragment (a) from the other peptide fragments (b) by selectively eluting the N-terminal peptide fragment (a) based on the difference in their reactivity or affinity to substrate; wherein
   the substrate comprises a molecule or part of a molecule that can chemically react with an amino group to form a covalent bond, and the separation step (3) is achieved by allowing the other peptide fragments (b) to bind to the substrate by the covalent bond while allowing the N-terminal peptide fragment (a) to elute.

4. The method according to claim 3, wherein the substrate is selected from the group consisting of p-phenylene diisothiocyanate (DITC) polymer resin, and allylamine polymer resin.

5. A method for selectively collecting the N-terminal peptide fragment of a protein, comprising:
   a protection step (1) of protecting side chain-amino groups of amino acid residues containing side chain-amino groups of a protein of interest modified on the N-terminus to obtain a protected protein protected on the side chain-amino groups;
   a fragmentation step (2) of cleaving the protected protein into one N-terminal peptide fragment (a) containing the N-terminus of the peptide of interest and one or more of peptide fragments (b) other than the N-terminal peptide fragment (a);
   a separation step (3) of separating the N-terminal peptide fragment (a) from the other peptide fragments (b) by selectively eluting the N-terminal peptide fragment (a) based on the difference in their reactivity or affinity to substrate; and
   after the fragmentation step (2) and before the separation step (3), the step of coupling an affinity compound with the N-terminuses of the other peptide fragments (b), the affinity compound capable of specifically binding to a particular molecule or a particular part of a molecule to form a complex, wherein the substrate includes an immobilized ligand comprising the particular molecule or the particular part of the molecule; wherein
   the separation step (3) is achieved by allowing the other peptide fragments (b) to bind to the substrate by a bond on forming the complex while allowing the N-terminal peptide fragment (a) to elute.

6. The method according to claim 5, wherein the affinity compound is an antigen and the ligand is an antibody against the antigen.

7. The method according to claim 5, wherein the affinity compound is a biotin derivative and the ligand is an avidin.

8. A method for selectively collecting the N-terminal peptide fragment of a protein, comprising:
- a fragmentation step (2') of cleaving a protein of interest modified on the N-terminus into one N-terminal peptide fragment (a') and one or more of peptide fragments (b') other than the N-terminal peptide fragment (a');
- a protection step (1') of protecting side chain-amino groups of amino acid residues containing side chain-amino group of the N-terminal peptide fragment (a') and the other peptide fragments (b') to obtain a protected N-terminal peptide fragment (a) protected on the side chain-amino groups, along with the other protected polypeptide fragments (b) protected on the side chain-amino groups; and
- a separation step (3) of separating the N-terminal peptide fragment (a) from the other peptide fragments (b) by selectively eluting the N-terminal peptide fragment (a) based on the difference in their reactivity or affinity to substrate; wherein
- the substrate comprises a molecule or part of a molecule that can chemically react with an amino group to form a covalent bond, and the separation step (3) is achieved by allowing the other peptide fragments (b) to bind to the substrate by the covalent bond while allowing the N-terminal peptide fragment (a) to elute.

9. The method according to claim 8, wherein the substrate is selected from the group consisting of p-phenylene diisothiocyanate (DITC) polymer resin, and allylamine polymer resin.

10. A method for selectively collecting the N-terminal peptide fragment of a protein, comprising:
- a fragmentation step (2') of cleaving a protein of interest modified on the N-terminus into one N-terminal peptide fragment (a') and one or more of peptide fragments (b') other than the N-terminal peptide fragment (a');
- a protection step (1') of protecting side chain-amino groups of amino acid residues containing side chain-amino group of the N-terminal peptide fragment (a') and the other peptide fragments (b') to obtain a protected N-terminal peptide fragment (a) protected on the side chain-amino groups, along with the other protected polypeptide fragments (b) protected on the side chain-amino groups;
- a separation step (3) of separating the N-terminal peptide fragment (a) from the other peptide fragments (b) by selectively eluting the N-terminal peptide fragment (a) based on the difference in their reactivity or affinity to substrate; and
- after the fragmentation step (2) and before the separation step (3), the step of coupling an affinity compound with the N-terminuses of the other peptide fragments (b), the affinity compound capable of specifically binding to a particular molecule or a particular part of a molecule to form a complex;
- wherein the substrate includes an immobilized ligand comprising the particular molecule or the particular part of the molecule, and the separation step (3) is achieved by allowing the other peptide fragments (b) to bind to the substrate by a bond on forming the complex while allowing the N-terminal peptide fragment (a) to elute.

11. The method according to claim 10, wherein the affinity compound is an antigen and the ligand is an antibody against the antigen.

12. The method according to claim 10, wherein the affinity compound is a biotin derivative and the ligand is an avidin.

13. A method for selectively collecting the N-terminal peptide fragment of a protein, comprising:
- a protection step (1) of protecting side chain-amino groups of amino acid residues containing side chain-amino groups of a protein of interest with unmodified N-terminus to obtain a protected protein protected on the side chain-amino groups;
- a fragmentation step (2) of cleaving the protected protein into one N-terminal peptide fragment (a) containing the N-terminus of the peptide of interest and one or more of peptide fragments (b) other than the N-terminal peptide fragment (a);
- a separation step (3) of separating the N-terminal peptide fragment (a) from the other peptide fragments (b) by selectively eluting the N-terminal peptide fragment (a) based on the difference in their reactivity or affinity to substrate; and
- after the protection step (1) and before the fragmentation step (2), the step of modifying the unmodified N-terminus of the protein of interest with an affinity compound that can specifically bind to a particular molecule or a particular part of a molecule to form a complex;
- wherein the separation step (3) is achieved by allowing the other peptide fragments (b) to bind to the substrate while allowing the N-terminal peptide fragment (a) to elute.

14. A method for selectively collecting the N-terminal peptide fragment of a protein, comprising:
- a protection step (1) of protecting side chain-amino groups of amino acid residues containing side chain-amino groups of a protein of interest with unmodified N-terminus to obtain a protected protein protected on the side chain-amino groups;
- a fragmentation step (2) of cleaving the protected protein into one N-terminal peptide fragment (a) containing the N-terminus of the peptide of interest and one or more of peptide fragments (b) other than the N-terminal peptide fragment (a);
- a separation step (3) of separating the N-terminal peptide fragment (a) from the other peptide fragments (b) by selectively eluting the N-terminal peptide fragment (a) based on the difference in their reactivity or affinity to substrate; and
- after the protection step (1) and before the fragmentation step (2), the step of modifying the unmodified N-terminus of the protein of interest with an affinity compound that can specifically bind to a particular molecule or a particular part of a molecule to form a complex;
- wherein the substrate comprises an immobilized ligand comprising the particular molecule or the particular part of the molecule, and the separation step (3) is achieved by allowing the N-terminal peptide fragment (a) to bind to the substrate by a bond on forming the complex while allowing the other peptide fragments (b) to elute and subsequently eluting the bound N-terminal peptide fragment (a).

15. The method according to claim 14, wherein the affinity compound is an antigen and the ligand is an antibody against the antigen.

16. The method according to claim 14, wherein the affinity compound is a biotin derivative and the ligand is an avidin.

17. The method according to claim 13, wherein the substrate comprises a molecule or a part of a molecule that can chemically react with an amino group to form a covalent bond, and the separation step (3) is achieved by allowing the other peptide fragments (b) to bind to the substrate by the covalent bond while allowing the N-terminal peptide fragment (a) to elute.

18. The method according to claim 17, wherein the substrate is selected from the group consisting of p-phenylene diisothiocyanate (DITC) polymer resin, and allylamine polymer resin.

19. A method for selectively collecting the N-terminal peptide fragment of a protein, comprising:
- a protection step (1) of protecting side chain-amino groups of amino acid residues containing side chain-amino groups of a protein of interest with unmodified N-terminus to obtain a protected protein protected on the side chain-amino groups;
- a fragmentation step (2) of cleaving the protected protein into one N-terminal peptide fragment (a) containing the N-terminus of the peptide of interest and one or more of peptide fragments (b) other than the N-terminal peptide fragment (a);
- a separation step (3) of separating the N-terminal peptide fragment (a) from the other peptide fragments (b) by selectively eluting the N-terminal peptide fragment (a) based on the difference in their reactivity or affinity to substrate; and
- after the protection step (1) and before the fragmentation step (2), the step of modifying the unmodified N-terminus of the protein of interest with a compound other than the affinity compounds that can specifically bind to a particular molecule or a particular part of a molecule to form a complex;
- wherein the substrate comprises a molecule or a part of a molecule that can chemically react with an amino group to form a covalent bond, the separation step (3) is achieved by allowing the other peptide fragments (b) to bind to the substrate by the covalent bond while allowing the N-terminal peptide fragment (a) to elute.

20. The method according to claim 19, wherein the substrate is selected from the group consisting of p-phenylene diisothiocyanate (DITC) polymer resin, and allylamine polymer resin.

21. A method for selectively collecting the N-terminal peptide fragment of a protein, comprising:
- a protection step (1) of protecting side chain-amino groups of amino acid residues containing side chain-amino groups of a protein of interest with unmodified N-terminus to obtain a protected protein protected on the side chain-amino groups;
- a fragmentation step (2) of cleaving the protected protein into one N-terminal peptide fragment (a) containing the N-terminus of the peptide of interest and one or more of peptide fragments (b) other than the N-terminal peptide fragment (a);
- a separation step (3) of separating the N-terminal peptide fragment (a) from the other peptide fragments (b) by selectively eluting the N-terminal peptide fragment (a) based on the difference in their reactivity or affinity to substrate; and
- after the protection step (1) and before the fragmentation step (2), the step of modifying the unmodified N-terminus of the protein of interest with a compound other than the affinity compounds that can specifically bind to a particular molecule or a particular part of a molecule to form a complex, and
- after the fragmentation step (2) and before the separation step (3), the step of coupling an affinity compound with the N-terminuses of the other peptide fragments (b), the affinity compound capable of specifically binding to a particular molecule or a particular part of a molecule to form a complex;
- wherein the substrate includes an immobilized ligand comprising the particular molecule or the particular part of the molecule, the separation step (3) is achieved by allowing the other peptide fragments (b) to bind to the substrate by a bond on forming the complex while allowing the N-terminal peptide fragment (a) to elute.

22. The method according to claim 21, wherein the affinity compound is an antigen and the ligand is an antibody against the antigen.

23. The method according to claim 21, wherein the affinity compound is a biotin derivative and the ligand is an avidin.

24. The method according to any of claims 1, 3, 5, 13, 19 and 21, wherein the protection step (1) is performed by guanidinating side chain-amino groups of amino acid residues containing side chain-amino groups of a protein of interest to obtain a guanidinated protein in which the side chain-amino groups have been converted to guanidino groups.

25. The method according to any of claims 2, 8 and 10, wherein the protection step (1') is performed by guanidinating side chain-amino groups of amino acid residues containing side chain-amino groups of the N-terminal peptide fragment (a') and the other peptide fragments (b') to obtain a guanidinated N-terminal peptide fragment (a) in which the side chain-amino groups have been converted to guanidino groups, along with the other guanidinated polypeptide fragments (b) in which the side chain-amino groups have been converted to guanidino groups.

* * * * *